United States Patent
Nedergaard et al.

(10) Patent No.: US 11,634,479 B2
(45) Date of Patent: Apr. 25, 2023

(54) IMMUNOASSAY FOR COLLAGEN TYPE VI

(71) Applicant: Nordic Bioscience A/S, Herlev (DK)

(72) Inventors: Anders Nedergaard, Copenhagen (DK); Jannie Marie Sand, Malov (DK); Shu Sun, Farum (DK); Diana Julie Oersnes-Leeming, Klampenborg (DK); Kim Henriksen, Hillerod (DK)

(73) Assignee: Nordic Bioscience A/S, Herlev (DK)

( * ) Notice: Subject to any disclaimer, the term of this patent is extended or adjusted under 35 U.S.C. 154(b) by 891 days.

(21) Appl. No.: 16/431,979

(22) Filed: Jun. 5, 2019

(65) Prior Publication Data
US 2019/0309055 A1 Oct. 10, 2019

Related U.S. Application Data

(63) Continuation-in-part of application No. 15/563,607, filed as application No. PCT/EP2016/057127 on Mar. 31, 2016.

(30) Foreign Application Priority Data

Apr. 1, 2015 (GB) ..................................... 1505654

(51) Int. Cl.
*G01N 33/53* (2006.01)
*C07K 16/18* (2006.01)
*G01N 33/68* (2006.01)

(52) U.S. Cl.
CPC ............. *C07K 16/18* (2013.01); *G01N 33/68* (2013.01); *C07K 2317/32* (2013.01); *C07K 2317/34* (2013.01); *C07K 2317/565* (2013.01); *G01N 2333/78* (2013.01)

(58) Field of Classification Search
CPC C07K 16/18; C07K 2317/32; C07K 2317/34; C07K 2317/565; G01N 33/68; G01N 2333/78; G01N 33/6893; G01N 33/6887; G01N 2470/00; G01N 2470/04; G01N 2470/06; G01N 2470/10; G01N 2470/12
See application file for complete search history.

(56) References Cited

FOREIGN PATENT DOCUMENTS

| JP | 2009168669 A | 7/2009 |
|----|--------------|--------|
| WO | 2005019825 A2 | 3/2005 |

OTHER PUBLICATIONS

Kalluri et al., PNAS 1994;91(13):6201-6205.*
Barascuk et al. (2013) A MMP derived versican neo-epitope is elevated in plasma from patients with atherosclerotic heart disease. Int J Clin Exp Med; 6: 174-184.
Bedogni et al. (2006) The Fatty Liver Index: a simple and accurate predictor of hepatic steatosis in the general population. BMC Gastroenterol; 6:33.
Belavy et al. (2009) Resistive vibration exercise reduces lower limb muscle atrophy during 56-day bed-rest. Journal of Musculoskeletal & Neuronal Interactions; 9:225-235.
Bhasin et al. (2009) N-terminal propeptide of type III procollagen as a biomarker of anabolic response to recombinant human GH and testosterone. J Clin Endocrinol Metab; 94:4224-4233.
Bidanset et al. (1992) Binding of the proteoglycan decorin to collagen type VI. J Biol Chem.; 267: 5250-6.
Bonaldo P, Sandri M (2012) Cellular and molecular mechanisms of muscle atrophy. Dis Model Mech.; 6:25-39.
Carter et al. (2013) Aalpha-Val360: a marker of neutrophil elastase and COPD disease activity. Eur Respir J.; 41: 31-38.
Charbonnel et al. (2010) Pioglitazone use in combination with insulin in the prospective pioglitazone clinical trial in macrovascular events study (PROactive19). J Clin Endocrinol Metab.; 95:2163-71.
Chen et al. (2011) Evaluation of early biomarkers of muscle anabolic response to testosterone. J Cachexia Sarcopenia Muscle; 2:45-56.
Corhay et al. (2014) Increased of exhaled breath condensate neutrophil chemotaxis in acute exacerbation of COPD. Respir Res.; 15:115.
Cox TR, Erler JT. (2011) Remodeling and homeostasis of the extracellular matrix: implications for fibrotic diseases and cancer. Dis Model Mech.; 4:165-178.
Cruz-Jentoft et al. (2010) Sarcopenia: European consensus on definition and diagnosis: Report of the European Working Group on Sarcopenia in Older People. Age Ageing; 39: 412-23.
Dankel et al. (2014) COL6A3 expression in adipocytes associates with insulin resistance and depends on PPARgamma and adipocyte size. Obesity (Silver Spring); 22:1807-13.
Donaldson et al. (2002) Relationship between exacerbation frequency and lung function decline in chronic obstructive pulmonary disease. Thorax; 57:847-852.
Donaldson GC, Wedzicha JA. (2006) COPD exacerbations .1: Epidemiology. Thorax; 61:164-168.

(Continued)

*Primary Examiner* — Carmencita M Belei
(74) *Attorney, Agent, or Firm* — Benjamin Aaron Adler

(57) ABSTRACT

The present invention provides an immunological binding partner reactive with a C-terminal epitope of the C5 domain of the α3 chain of collagen Type 6, and a method of immunoassay using the immunological binding partner for detecting and quantifying the C-terminal epitope. The invention also provides a method of investigating the rate of formation of extracellular matrix and a method for identifying a subject suitable for treatment with an insulin sensitizer.

11 Claims, 12 Drawing Sheets
Specification includes a Sequence Listing.

(56) References Cited

OTHER PUBLICATIONS

Engvall et al. (1986) Molecular assembly, secretion, and matrix deposition of type VI collagen. J Cell Biol.; 102: 703-710.

Granzier HL, Irving TC. (1995) Passive tension in cardiac muscle: contribution of collagen, titin, microtubules, and intermediate filaments. Biophys J.; 68:1027-44.

Hallgren et al. (2010) Altered fibroblast proteoglycan production in COPD. Respir. Res.; 11:55.

Heinemeier et al. (2009) Effect of unloading followed by reloading on expression of collagen and related growth factors in rat tendon and muscle. J Appl Physiol.; 106:178-186.

Hortobagyi et al. (2000) Changes in muscle strength, muscle fibre size and myofibrillar gene expression after immobilization and retraining in humans. J Physiol.; 524:293-304.

Huang et al. (2006) Inhibition of versican synthesis by antisense alters smooth muscle cell phenotype and induces elastic fiber formation in vitro and in neointima after vessel injury. Circ. Res.; 98:370-377.

Hughes et al. (2002) Longitudinal changes in body composition in older men and women: role of body weight change and physical activity. Am. J. Clin. Nutr.; 76:473-81.

Hurst et al. (2010) Susceptibility to exacerbation in chronic obstructive pulmonary disease. N. Engl. J. Med.; 363: 1128-1138.

Karsdal et al. (2015) Novel insights into the function and dynamics of extracellular matrix in liver fibrosis. Am J Physiol Gastrointest Liver Physiol.; 308:G807-G830.

Karsdal et al. (2013) Extracellular matrix remodeling: the common denominator in connective tissue diseases. Possibilities for evaluation and current understanding of the matrix as more than a passive architecture, but a key player in tissue failure. Assay Drug Dev. Technol.; 11: 70-92.

Keene et al.(1988) Ultrastructure of type VI collagen in human skin and cartilage suggests an anchoring function for this filamentous network. J Cell Biol.; 107:1995-2006.

Kenagy et al. (2006) Versican degradation and vascular disease. Trends Cardiovasc Med.; 16:209-215.

Khan et al. (2009) Metabolic dysregulation and adipose tissue fibrosis: role of collagen VI. Mol Cell Biol.; 29:1575-91.

Kuo et al. (1997) Type VI collagen anchors endothelial basement membranes by interacting with type IV collagen. J Biol Chem.; 272:26522-9.

Lampe AK, Bushby KMD (2005) Collagen VI related muscle disorders. J Med Genet.; 42:673-685.

Lebenszte JN et al. (2006) Matrix-derived serum markers in monitoring liver fibrosis in children with chronic hepatitis B treated with interferon alpha. World J Gastroenterol.; 2:3338-43.

Leeming et al. (2012) Serological investigation of the collagen degradation profile of patients with chronic obstructive pulmonary disease or idiopathic pulmonary fibrosis. Biomark Insights; 7:119-126.

Leeming et al. (2013) Novel serological neo-epitope markers of extracellular matrix proteins for the detection of portal hypertension. Aliment Pharmacol Ther.; 38:1086-96.

Mak et al. (2014) Type VI Collagen: Its Biology and Value as a Biomarker of Hepatic Fibrosis. Austin Biomark Diagn.; 1:9.

Merrilees et al. (2008) Changes in elastin, elastin binding protein and versican in alveoli in chronic obstructive pulmonary disease. Respir Res; doi: 10.1186/1465-9921-9-41.

Mercer et al. (2005) MMP-9, TIMP-1 and inflammatory cells in sputum from COPD patients during exacerbation. Respir Res.; 6:151.

Miller et al. (2005) Coordinated collagen and muscle protein synthesis in human patella tendon and quadriceps muscle after exercise. J Physiol.(Lond); 567:1021-1033.

Miller et al. (2001) Hindlimb unloading induces a collagen isoform shift in the soleus muscle of the rat. AJP: Regulatory, Integrative and Comparative Physiology; 281:R1710-R1717.

Nedergaard et al. (2013) Type VI collagen turnover-related peptides—novel serological biomarkers of muscle mass and anabolic response to loading in young men. J Cachexia Sarcopenia Muscle; 4:267-275.

Nedergaard et al. (2013) Serological muscle loss biomarkers: an overview of current concepts and future possibilities. J Cachexia Sarcopenia Muscle; 4:1-17.

Nielsen et al. (2013) The neo-epitope specific PRO-C3 ELISA measures true formation of type III collagen associated with liver and muscle parameters. Am J Transl.Res.; 5:303-315.

Niemela et al. (1985) Purification and characterization of the N-terminal propeptide of human type III procollagen. Biochem J.; 232:145-50.

O'Reilly (2013) Sputum PGP is reduced by azithromycin treatment in patients with COPD and correlates with exacerbations. BMJ Open; 3:e004140.

Orkin et al. (1977) A murine tumor producing a matrix of basement membrane. J Exp. Med.; 145: 204-220.

Pasarica et al. (2009) Adipose tissue collagen VI in obesity. J Clin. Endocrinol. Metab.; 94:5155-62.

Park J, Scherer PE. (2012) Adipocyte-derived endotrophin promotes malignant tumor progression. J Clin. Invest.; 122:4243-56.

Park J, Scherer PE. (2013) Endotrophin in the tumor stroma: a new therapeutic target for breast cancer? Expert Rev Anticancer Ther.; 13:111-3.

Pfister et al. (1995) Identification and synthesis of chemotactic tripeptides from alkali-degraded whole cornea. A study of N-acetyl-proline-glycine-proline and N-methyl-proline-glycine-proline. Invest Ophthalmol. Vis. Sci.; 36: 1306-1316.

Ruhl et al. (1999) Soluble collagen VI drives serum-starved fibroblasts through S phase and prevents apoptosis via down-regulation of Bax. J Biol Chem.; 274:34361-34368.

Sand et al. (2013) MMP mediated degradation of type IV collagen alpha 1 and alpha 3 chains reflects basement membrane remodeling in experimental and clinical fibrosis—validation of two novel biomarker assays. PLoS One; 8: e84934.

Lamande et al. (2006) The C5 domain of the collagen VI alpha3(VI) chain is critical for extracellular microfibril formation and is present in the extracellular matrix of cultured cells. J Biol Chem.; 281:16607-14.

Scharf G, Heineke J. (2012) Finding good biomarkers for sarcopenia. J Cachexia Sarcopenia Muscle; 3:145-8.

Seemungal et al. (1998) Effect of exacerbation on quality of life in patients with chronic obstructive pulmonary disease. Am J Respir Crit Care Med.; 157:1418-1422.

Soler-Cataluna et al. (2005) Severe acute exacerbations and mortality in patients with chronic obstructive pulmonary disease. Thorax; 60:925-931.

Soroceanu et al. (2004) Rosiglitazone impacts negatively on bone by promoting osteoblast/osteocyte apoptosis. J Endocrinol.; 183:203-16.

Stallcup et al. (1990) Interaction of the NG2 chondroitin sulfate proteoglycan with type VI collagen. J Cell Biol.; 111: 3177-88.

Sun et al. (2014) Endotrophin triggers adipose tissue fibrosis and metabolic dysfunction. Nat Commun.; 5:3485.

Tapanainen et al. (1997) Collagen metabolites in the prediction of response to GH therapy in short children. Eur J Endocrinol.; 137:621-625.

Urciuolo et al. (2013) Collagen VI regulates satellite cell self-renewal and muscle regeneration. Nat Commun.; 4:1964. doi: 10.1038/ncomms2964.

Veidal et al. (2011) MMP mediated degradation of type VI collagen is highly associated with liver fibrosis—identification and validation of a novel biochemical marker assay. PLoS One; 6:e24753.

Vestbo J, Rennard S. (2010) Chronic obstructive pulmonary disease biomarker(s) for disease activity needed urgently. Am J Respir Crit Care Med.; 182: 863-864.

Sand et al. (2015) Accelerated extracellular matrix turnover during exacerbations of COPD. Respir Res.; 16:69.

Sun et al. (2015) Collagen Type III and VI Turnover in Response to Long-Term Immobilization. PLoS One.; 10(12): e0144525. doi: 10.1371/journal.pone.0144525.

Barascuk et al. (2010) A novel assay for extracellular matrix remodeling associated with liver fibrosis: An enzyme-linked

(56) References Cited

OTHER PUBLICATIONS immunosorbent assay (ELISA) for a MMP-9 proteolytically revealed neo-epitope of type III collagen. Clin Biochem.; 43: 899-904.
Getter et al. (1977) A simple method for polyethylene glycol-promoted hybridization of mouse myeloma cells. Somatic Cell Genet .; 3:231-6.
Feigh et al. (2011) A novel oral form of salmon calcitonin improves glucose homeostasis and reduces body weight in diet-induced obese rats. Diabetes Obes. Metab.; 13:911-20.
Geise et al. (2003) Collagens—structure, function, and biosynthesis. Adv Drug Deliv.; 55:1531-46.
Agrawal et al. (2012) Balaglitazone: a second generation peroxisome proliferator-activated receptor (PPAR) gamma (gamma) agonist. Mini Rev Med Chem.; 12:87-97.
Aigner et al. (2002) The C5 domain of Col6A3 is cleaved off from the Col6 fibrils immediately after secretion. Biochem Biophys Res Commun.; 290:743-8.
Armbrecht et al. (2010) Resistive vibration exercise attenuates bone and muscle atrophy in 56 days of bed rest: biochemical markers of bone metabolism. Osteoporos Int. 21:597-607.
Atkinson et al. (1996) Collagen VI regulates normal and transformed mesenchymal cell proliferation in vitro. Exp Cell Res.; 228:283-291.
Berger et al. (2005) PPARs: therapeutic targets for metabolic disease. Trends Pharmacol Sci.; 26:244-51.
Bonaldo et al. (1990) Structural and functional features of the alpha 3 chain indicate a bridging role for chicken collagen VI in connective tissues. Biochemistry; 29:1245-54.
Burt et al. (1990) Ultrastructural localization of extracellular matrix proteins in liver biopsies using ultracryomicrotomy and immunogold labelling. Histopathology; 16:53-8.
Bushby et al. (2014) Collagen type VI myopathies. Adv Exp Med Biol.; 802:185-99.
Cho N, Momose Y. (2008) Peroxisome proliferator-activated receptor gamma agonists as insulin sensitizers: from the discovery to recent progress. Curr Top Med Chem. 8:1483-507.
Giannelli et. (2005) Matrix metalloproteinase imbalance in muscle disuse atrophy. Histol Histopathol.; 20: 99-106.
Global Initiative for Chronic Obstructive Lung Disease (GOLD). Global Strategy for the Diagnosis, Management and Prevention of COPD. www.goldcopd.org. Date last updated: Jan. 2014. Date last accessed: Oct. 22, 2014.
Griffiths et al. (1992) Light microscopic and ultrastructural distribution of type VI collagen in human liver: alterations in chronic biliary disease. Histopathology; 21:335-44.
Henriksen et al. (2011) Efficacy and safety of the PPARgamma partial agonist balaglitazone compared with pioglitazone and placebo: a phase III, randomized, parallel-group study in patients with type 2 diabetes on stable insulin therapy. Diabetes Metab. Res Rev.; 27:392-401.
Home et al. (2009) Rosiglitazone evaluated for cardiovascular outcomes in oral agent combination therapy for type 2 diabetes (RECORD): a multicentre, randomised, open-label trial. Lancet; 373:2125-35.
Karalliedde J, Buckingham RE. (2007) Thiazolidinediones and their fluid-related adverse effects: facts, fiction and putative management strategies. Drug Saf.; 30:741-53.
Karsdal et al. (2011) Protein fingerprints—relying on and understanding the information of serological protein measurements. Clin Biochem.; 44:1278-1279.
Larsen et al. (2018) Dissociation of antihyperglycaemic and adverse effects of partial perioxisome proliferator-activated receptor (PPAR-gamma) agonist balaglitazone. Eur J Pharmacol.; 596:173-9.
Leeming et al. (2012) Enzyme-linked immunosorbent serum assay specific for the 7S domain of Collagen Type IV (P4NP 7S): A marker related to the extracellular matrix remodeling during liver fibrogenesis. Hepatol Res.; 42:482-493.
Rennie et al. (2010) Facts, noise and wishful thinking: muscle protein turnover in aging and human disuse atrophy. Scand J Med Sci Sports; 20:5-9.
Reznick et al. (2003) Expression of matrix metalloproteinases, inhibitor, and acid phosphatase in muscles of immobilized hindlimbs of rats. Muscle Nerve; 27:51-9.
Rittweger et al. (2006) Highly demanding resistive vibration exercise program is tolerated during 56 days of strict bed-rest. Int J Sports Med.; 27:553-9.
Ruhl et al. (1999) Soluble collagen VI induces tyrosine phosphorylation of paxillin and focal adhesion kinase and activates the MAP kinase erk2 in fibroblasts. Exp Cell Res.; 250:548-557.
Savolainen et al. (1987) Effect of immobilization on collagen synthesis in rat skeletal muscles. American Journal of Physiology—Regulatory, Integrative and Comparative Physiology; 252:R883-R888.
Stickel et al. (2001) Serum collagen type VI and XIV and hyaluronic acid as early indicators for altered connective tissue turnover in alcoholic liver disease. Dig Dis Sci.; 46:2025-32.
Takada et al. (2007) Suppression of PPAR transactivation switches cell fate of bone marrow stem cells from adipocytes into osteoblasts. Ann N Y Acad Sci.; 1116:182-95.
Takamatsu et al. (1997) Noninvasive determination of liver collagen content in chronic hepatitis. Multivariate regression modeling with blood chemical parameters as variables. J Gastroenterol.; 32:355-360.
Tetley TD. (2005) Inflammatory cells and chronic obstructive pulmonary disease. Curr Drug Targets Inflamm Allergy; 4:607-618.
Welles S. (2002) Cellular and molecular basis of age-related sarcopenia. Can J Appl Physiol; 27:19-41.
Williams P, Goldspink G. (1981) Connective tissue changes in surgically overloaded muscle. Cell Tissue Res.; 221:465-470.
Corada et al. (2001) Monoclonal antibodies directed to different regions of vascular endothelial cadherin extracellular domain affect adhesion and clustering of the protein and modulate endothelial permeability. Blood; 97:1679-84.
Padlan E.A. (1996) X-ray crystallography of antibodies. Adv Protein Chem.; 49:57-133.

* cited by examiner

SEQUENCE LISTING

```
<160> NUMBER OF SEQ ID NOS: 13

<210> SEQ ID NO 1
<211> LENGTH: 10
<212> TYPE: PRT
<213> ORGANISM: Homo sapiens
<220> FEATURE:
<223> OTHER INFORMATION: C-terminal epitope of Collagen Type VI

<400> SEQUENCE: 1

Lys Pro Gly Val Ile Ser Val Met Gly Thr
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Elongated Sequence

<400> SEQUENCE: 2

Lys Pro Gly Val Ile Ser Val Met Gly Thr Ala
1               5                   10
```

<210> SEQ ID NO 3
<211> LENGTH: 9
<212> TYPE: PRT
<213> ORGANISM: Artificial Sequence
<220> FEATURE:
<223> OTHER INFORMATION: Truncated Sequence

<400> SEQUENCE: 3

Lys Pro Gly Val Ile Ser Val Met Gly
1               5

<210> SEQ ID NO 4
<211> LENGTH: 10
<212> TYPE: PRT
<213> ORGANISM: Artificial Sequence
<220> FEATURE:
<221> NAME/KEY: SITE
<222> LOCATION: 1
<223> OTHER INFORMATION: Biotinylated with optional linker
<220> FEATURE:
<223> OTHER INFORMATION: Biotinylated with optional linker

<400> SEQUENCE: 4

Lys Pro Gly Val Ile Ser Val Met Gly Thr
1               5                   10

<210> SEQ ID NO 5
<211> LENGTH: 440
<212> TYPE: PRT
<213> ORGANISM: Artificial Sequence
<220> FEATURE:
<223> OTHER INFORMATION: Heavy chain sequence of mouse IgG1 isotype of
      monoclonal antibody 10A3

<400> SEQUENCE: 5

Glu Val Gln Leu Gln Gln Ser Gly Pro Val Met Val Lys Pro Gly Thr
1               5                   10                  15

Ser Val Lys Thr Ser Cys Lys Ala Ser Gly Tyr Thr Phe Thr Asp Phe
            20                  25                  30

Asn Met Asn Trp Val Lys Gln Ser His Gly Lys Ser Leu Glu Trp Ile
        35                  40                  45

Gly Ala Ile Asn Pro His Asn Gly Ala Thr Ser Tyr Asn Gln Lys Phe
    50                  55                  60

Ser Gly Lys Ala Thr Leu Thr Val Asp Lys Ser Ser Ser Thr Ala Tyr
65                  70                  75                  80

Met Glu Leu Asn Ser Leu Thr Ser Asp Asp Ser Ala Val Tyr Tyr Cys
                85                  90                  95

Ala Arg Trp Gly Asn Gly Lys Asn Ser Trp Gly Gln Gly Thr Thr Leu
            100                 105                 110

Thr Val Ser Ser Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
            210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
                260                 265                 270

Asp Asp Val Glu Val His Thr Ala Gln Thr Gln Pro Arg Glu Glu Gln
            275                 280                 285

Phe Asn Ser Thr Phe Arg Ser Val Ser Glu Leu Pro Ile Met His Gln
            290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Lys Glu Gln Met Ala
            340                 345                 350

Lys Asp Lys Val Ser Leu Thr Cys Met Ile Thr Asp Phe Phe Pro Glu
            355                 360                 365

Asp Ile Thr Val Glu Trp Gln Trp Asn Gly Gln Pro Ala Glu Asn Tyr
370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
            420                 425                 430

Ser Leu Ser His Ser Pro Gly Lys
        435                 440

<210> SEQ ID NO 6
<211> LENGTH: 5
<212> TYPE: PRT
<213> ORGANISM: Artificial Sequence
<220> FEATURE:
<223> OTHER INFORMATION: Sequence of heavy chain complementarity-
      determining region CDR-H1 of 10A3 monoclonal antibody

<400> SEQUENCE: 6

Asp Phe Asn Met Asn
1               5

<210> SEQ ID NO 7
<211> LENGTH: 17
<212> TYPE: PRT
<213> ORGANISM: Artificial Sequence
<220> FEATURE:
<223> OTHER INFORMATION: Sequence of heavy chain complementarity-
      determining region CDR-H2 of 10A3 monoclonal antibody

<400> SEQUENCE: 7

Ala Ile Asn Pro His Asn Gly Ala Thr Ser Tyr Asn Gln Lys Phe Ser
1               5                   10                  15

Gly

<210> SEQ ID NO 8
<211> LENGTH: 7

```
<212> TYPE: PRT
<213> ORGANISM: Artificial Sequence
<220> FEATURE:
<223> OTHER INFORMATION: Sequence of heavy chain complementarity-
      determining region CDR-H3 of 10A3 monoclonal antibody

<400> SEQUENCE: 8

Trp Gly Asn Gly Lys Asn Ser
1               5

<210> SEQ ID NO 9
<211> LENGTH: 219
<212> TYPE: PRT
<213> ORGANISM: Artificial Sequence
<220> FEATURE:
<223> OTHER INFORMATION: Light chain sequence of mouse Kappa isotype of
      monoclonal antibody 10A3

<400> SEQUENCE: 9

Asp Val Val Met Thr Gln Thr Pro Leu Ser Leu Pro Val Asn Leu Gly
1               5                   10                  15

Asp Gln Ala Ser Ile Ser Cys Arg Ser Ser Gln Arg Ile Val His Ser
                20                  25                  30

Asn Gly Ile Thr Phe Leu Glu Trp Tyr Leu Gln Lys Pro Gly Gln Ser
            35                  40                  45

Pro Lys Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Arg Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 10
<211> LENGTH: 16
<212> TYPE: PRT
<213> ORGANISM: Artificial Sequence
<220> FEATURE:
<223> OTHER INFORMATION: Sequence of light chain complementarity-
      determining region CDR-L1 of 10A3 monoclonal antibody

<400> SEQUENCE: 10

Arg Ser Ser Gln Arg Ile Val His Ser Asn Gly Ile Thr Phe Leu Glu
1               5                   10                  15
```

```
<210> SEQ ID NO 11
<211> LENGTH: 7
<212> TYPE: PRT
<213> ORGANISM: Artificial Sequence
<220> FEATURE:
<223> OTHER INFORMATION: Sequence of light chain complementarity-
      determining region CDR-L2 of 10A3 monoclonal antibody

<400> SEQUENCE: 11

Arg Val Ser Asn Arg Phe Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Sequence of light chain complementarity-
      determining region CDR-L3 of 10A3 monoclonal antibody

<400> SEQUENCE: 12

Phe Gln Gly Ser His Val Pro Leu Thr
1               5

<210> SEQ ID NO 13
<211> LENGTH: 10
<212> TYPE: PRT
<213> ORGANISM: Artificial Sequence
<220> FEATURE:
<223> OTHER INFORMATION: N-terminal epitope of MMP degraded collagen
      type VI fragment

<400> SEQUENCE: 13

Tyr Arg Gly Pro Glu Gly Pro Gln Gly Pro
1               5                   10
```

IMMUNOASSAY FOR COLLAGEN TYPE VI

FIELD OF THE INVENTION

The present invention relates to an antibody which binds to an epitope present at the C-terminus of the collagen type VI α3 chain and to immunoassays detecting said epitope.

BACKGROUND

Muscle mass and function is lost with age, a range of pathologies, and inactivity, and frequently due to a combination of the three. It is reported that individuals lose 1-2% skeletal muscle per year from $50^{th}$ years old (Hughes), that 2-3% of muscle mass is lost per week during immobilization (Hortobagyi et al. 2000), and even quicker with cachexia. Impaired muscle function in elderly or hospitalized individuals is associated with (co)morbidity and mortality (Cruz-Jentoft). With the increasing population age in the industrialized world, maintaining functional independence is therefore becoming of increasing importance. The diagnosis and management methods for muscle loss still rely on the imaging examination, e.g. magnetic resonance imaging (MRI), computed tomography (CT) and dual-energy X-ray absorptiometry (DXA) (Cruz-Jentoft). However, such examinations are either expensive or inconvenient to be used in routine clinical practice. Urinary and serological biomarkers such as creatinine and 3-methylhistidine are also used to assist the management of muscle loss. However, high variation and poor validity of these assays limit their use (Nedergaard 2013). In summary, there is an urgent need for biomarkers which can be used in the diagnosing and prognosing muscle function as well as monitoring anti-catabolic treatment outcomes (Sharf).

Loss of muscle mass is driven by unbalanced turnover of muscle extracellular proteins (Rennie 2010 and Welle 2002). As protein turnover, particularly of extracellular proteins, can allow proteolytic fragments to escape into the circulation, quantitative or qualitative changes in protein metabolism can give rise to biomarker profiles that can be of use in monitoring muscle mass or function (Nedergaard 2013).

Collagens are important extracellular proteins of skeletal muscle, which could contribute to the passive tension of muscle (Granzier).

Type III collagen is expressed in most of the type I collagen containing tissues except for bone, and is an important components of connective tissues, muscle tissues and skin et al (Gelse). PIIINP is the N-terminal propeptide of collagen type III, which is removed during mature type III collagen synthesis (Niemela). It has been reported to be related to the anabolic response of hormone treatment (Bhasin 2009 and Chen 2011). Recently, a new ELISA kit was developed by applying monoclonal antibody targeting the N-protease cleavage site of N-terminal procollagen, which could assess the true synthesis of type III collagen (Nielsen 2013).

Collagen Type VI is a unique extracellular collagen which can form an independent microfibrillar network in the basement membrane of cells. It can interact with other matrix proteins including collagens, biglycan, and proteoglycans (Kuo 1997, Bidanset 1992 and Stallcup 1990). In muscle, type VI collagen is part of the sarcolemma and is involved in anchoring the muscle fiber into the intramuscular extracellular matrix, and so is involved in force transmission (Bonaldo 1990 and Keene 1988). Moreover, mutations in type VI collagen can cause Bethlem myopathy and Ullrich congenital muscular dystrophy (Lampe). It has been reported that C-terminal of type VI collagen α3 chain is cleaved off from the mature type VI microfibril after secretion (Aigner 2002 and Lamande 2006).

However, Type VI collagen is not just involved in muscles and muscle loss.

Chronic obstructive pulmonary disease (COPD) is a heterogeneous, slow progressing disease characterized by persistent airflow limitation resulting from chronic inflammation, structural changes, and small airway narrowing (Global initiative . . . ). The main structural proteins of the extracellular matrix (ECM) of the lung are collagens, elastin, and proteoglycans. ECM remodelling is part of healthy tissue maintenance, where old proteins are degraded and new proteins formed (Cox). However, excessive ECM remodelling drives the structural changes in COPD promoting loss of lung function. A key challenge in COPD is the identification of biomarkers of disease progression (Vestbo). ECM investigation by assessment of lung structural proteins may provide biomarkers of disease activity and prognosis.

Exacerbations are periods of increased disease activity that drive COPD progression by accelerating loss of lung function (Donaldson 2002)), reducing quality of life (Seemungal), and causing mortality (Sofer-Cataluna). Patients in all COPD stages may experience exacerbations, although they become more frequent with increasing disease severity (Hurst). It is difficult to predict their occurrence, and the best predictor of future exacerbations is an exacerbation history (Hurst 2010 and Donaldson 2006). Although exacerbations are key events in COPD pathogenesis, little is known regarding structural changes in lung tissue during these events. Matrix metalloproteinase 9 (MMP-9) levels are known to be elevated while tissue inhibitor of metalloproteinase 1 (TIMP-1) levels are decreased in sputum of COPD patients at time of exacerbation compared to stable COPD (Mercer), suggesting a destructive environment.

Recent research has revealed that the ECM harbors properties of an endocrine organ, with its structural proteins generating signaling molecules that can modulate cellular processes at distant sites, including cell migration, differentiation, and angiogenesis. These molecules include the potent anti-angiogenic peptide endostatin, which is derived from type XVIII collagen, as well as tumstatin, vastatin, and restin, which are released from types IV, VII, and XV collagens, respectively (Karsdal, 2015).

The microflamentous interstitial type VI collagen, a triple helical molecule composed of the constituent chains α1(VI), α2(VI), and α3(VI), is expressed in most connective tissues and prominently in adipose tissue (Park, 2012), where it anchors cells through its interconnections with other ECM proteins (Mak, 2012). During formation of the microfilaments, its triple-helical core is proteolytically released from its pro-peptide (Aigner, 2002; Lamande, 2006). Here, further cleavage of the C-terminal pro-peptide of the α3(VI) chain generates endotrophin (herein referred to as "Pro-C6"), a newly identified adipokine. Endotrophin is prominently produced by adipose tissue and induces upregulation of transforming growth factor beta (TGF-β), adipose tissue fibrosis, angiogenesis, inflammation and, in animal models, has been shown to unfavorably modulate several metabolic functions such as insulin sensitivity, food intake, energy balance, and adipose tissue inflammation (Sun, 2014; Dankel, 2014; Park, 2013; Khan, 2009; Pasarica, 2009). These findings suggest that levels of endotrophin in blood may be useful for classifying and/or monitoring patients with metabolic dysfunction, especially those with type 2 diabetes.

Thiazolidinediones (TZDs) are peroxisome proliferator-activated receptor gamma (PPARγ) agonists and have been used widely to treat type 2 diabetes due to their ability to improve insulin sensitivity, lower glucose levels, and reduce the need for insulin (Cho, 2008; Charbonnel, 2010). However, the use of TZDs such as pioglitazone has been limited substantially by associated adverse effects (AEs) such as heart failure (Home, 2009), weight gain (Takada, 2007), peripheral oedema (Karalliedde, 2007), and bone loss in women (Soroceanu, 2004). In an attempt to minimize the AEs of PPARγ agonists, partial activators of PPARγ that trigger only a subset of PPARγ downstream signals, such as balaglitazone, have been developed (Berger, 2005; Agrawal, 2012). Such partial agonists achieve good glycemic control with reduced AEs (Larsen, 2008). A serum biomarker that would optimally define treatment responders could further improve efficacy and safety of such glitazones.

SUMMARY

We have now developed a monoclonal antibody and an ELISA kit targeting the C-terminal of α3 chain. We refer to this kit and to reactivity measured with it herein as 'Pro-C6'.

We have established that levels of Pro-C6 reflect the rate of muscle turnover and also that ECM remodelling, assessed systemically by biomarkers of protein remodelling fragments, is accelerated during an exacerbation of COPD where disease activity is high.

We have also established that elevated serum levels of endotrophin (i.e. "Pro-C6") predict response to two insulin sensitizers (Balaglitazone and Pioglitazone) and lower side-effects, identifying those patients with diabetes type II that profit from PPARγ agonist treatment.

The present invention now provides an immunological binding partner reactive with a C-terminal epitope of the C5 domain of the α3 chain of collagen Type VI.

Preferably said immunological binding partner specifically binds to a said C-terminal epitope comprised in a C-terminal amino acid sequence . . . KPGVISVMGT-COOH (SEQ ID. NO:1).

Said immunological binding partner is a monoclonal or polyclonal antibody. The immunological binding partner may be an antibody fragment with binding specificity as further explained below.

Preferably, said immunological binding partner does not recognise or bind an elongated version of said C-terminal amino acid sequence which is . . . KPGVISVMGTA (SEQ ID. NO:2)-COOH.

Preferably, said immunological binding partner does not recognise or bind (or also does not recognise or bind) a truncated version of said C-terminal amino acid sequence which is . . . KPGVISVMG-COOH (SEQ ID. NO:3).

Preferably still, the ratio of the affinity of said antibody for amino acid sequence . . . KPGVISVMGT-COOH (SEQ ID. NO:1) to the affinity of said antibody for elongated amino acid sequence . . . KPGVISVMGTA-COOH (SEQ ID. NO:2), and or to the truncated amino acid sequence . . . KPGVISVMG-COOH (SEQ ID. NO:3), is greater than 10 to 1, More generally, the ratio of the affinity of said immunological binding partner for amino acid sequence . . . KPGVISVMGT-COOH (SEQ ID. NO:1) to the affinity of said immunological binding partner for said elongated amino acid sequence is preferably greater than 10 to 1, preferably greater than 50 to 1, preferably greater than 100 to 1, preferably greater than 500 to 1, preferably greater than 1000 to 1, and most preferably greater than 10,000 to 1.

Also preferably, the ratio of the affinity of said immunological binding partner for amino acid sequence . . . KPGVISVMGT-COOH (SEQ ID. NO:1) to the affinity of said immunological binding partner for said truncated amino acid sequence is greater than 10 to 1, preferably greater than 50 to 1, preferably greater than 100 to 1, preferably greater than 500 to 1, preferably greater than 1000 to 1, and most preferably greater than 10,000 to 1.

Preferably, said immunological binding partner is a monoclonal antibody or fragment thereof having specific binding affinity. Said monoclonal antibody or fragment thereof may preferably comprise one or more complementarity-determining regions (CDRs) selected from:

```
CDR-L1:
                                    (SEQ ID. NO: 10)
RSSQRIVHSNGITFLE

CDR-L2:
                                    (SEQ ID. NO: 11)
RVSNRFS

CDR-L3:
                                    (SEQ ID. NO: 12)
FQGSHVPLT

CDR-H1:
                                    (SEQ ID. NO: 6)
DFNMN

CDR-H2:
                                    (SEQ ID. NO: 7)
AINPHNGATSYNQKFSG

CDR-H3:
                                    (SEQ ID. NO: 8)
WGNGKNS.
```

Preferably the antibody or fragment thereof comprises at least 2, 3, 4, 5 or 6 of the above listed CDR sequences.

Preferably the monoclonal antibody or fragment thereof has a light chain variable region comprising the CDR sequences

```
CDR-L1:
                                    (SEQ ID. NO: 10)
RSSQRIVHSNGITFLE

CDR-L2:
                                    (SEQ ID. NO: 11)
RVSNRFS
and

CDR-L3:
                                    (SEQ ID. NO: 12)
FQGSHVPLT.
```

Preferably the monoclonal antibody or fragment thereof has a light chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics)

RSSQRIVHSNGITFLE_WYLQKPGQSPKLLI_RVSNRFS_GVPDRFSGSGSG_
_TDFTLKISRVEAEDLGLYYC_FQGSHVPLT (amino acids 24 to
102 of SEQ ID. NO: 9).

Preferably the monoclonal antibody or fragment thereof has a heavy chain variable region comprising the CDR sequences

CDR-H1:
(SEQ ID. NO: 6)
DFNMN

CDR-H2:
(SEQ ID. NO: 7)
AINPHNGATSYNQKFSG
and

CDR-H3:
(SEQ ID. NO: 8)
WGNGKNS.

Preferably the monoclonal antibody or fragment thereof has a heavy chain that comprises framework sequences between the CDRs, wherein said framework sequences are substantially identical or substantially similar to the framework sequences between the CDRs in the heavy chain sequence below (in which the CDRs are shown in bold and underlined, and the framework sequences are shown in italics)

DFNMN<i>WVKQSHGKSLEWIG</i>AINPHNGATSYNQKFSG<i>KATLTVDKSSSTAY MELNSLTSDDSAVYYCAR</i>WGNGKNS (amino acids 31 to 105 of SEQ ID. NO: 5).

As used herein, the framework amino acid sequences between the CDRs of an antibody are substantially identical or substantially similar to the framework amino acid sequences between the CDRs of another antibody if they have at least 70%, 80%, 90% or at least 95% similarity or identity. The similar or identical amino acids may be contiguous or non-contiguous.

The framework sequences may contain one or more amino acid substitutions, insertions and/or deletions. Amino acid substitutions may be conservative, by which it is meant the substituted amino acid has similar chemical properties to the original amino acid. A skilled person would understand which amino acids share similar chemical properties. For example, the following groups of amino acids share similar chemical properties such as size, charge and polarity: Group 1 Ala, Ser, Thr, Pro, Gly; Group 2 Asp, Asn, Glu, Gln; Group 3 His, Arg, Lys; Group 4 Met, Leu, Ile, Val, Cys; Group 5 Phe Thy Trp.

A program such as the CLUSTAL program to can be used to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention. Identity or similarity is preferably calculated over the entire length of the framework sequences.

In certain preferred embodiments, the monoclonal antibody or fragment thereof may comprise the light chain variable region sequence:

<i>DVVMTQTPLSLPVNLGDQASISC</i>RSSQRIVHSNGITFLE<i>WYLQKPGQSPK LLIY</i>RVSNRFS<i>GVPDRFSGSGSGTDFTLKISRVEAEDLGLYYC</i>FQGSHVP LT<i>FGAGTRLELK</i> (amino acids 1 to 112 of SEQ ID. NO: 9)

and/or the heavy chain variable region sequence:

<i>EVQLQQSGPVMVKPGTSVKTSCKASGYTFT</i>DFNMN<i>WVKQSHGKSLEWIG</i>A INPHNGATSYNQKFSG<i>KATLTVDKSSSTAYMELNSLTSDDSAVYYCAR</i>WG NGKNS<i>WGQGTTLTVSS</i> (amino acids 1 to 116 of SEQ ID. NO: 5)

(CDRs bold and underlined; Framework sequences in italics)

The invention includes a method of immunoassay for detecting in a sample a C-terminal epitope of the α3 chain of collagen type VI, wherein said method comprises contacting a sample comprising said C-terminal epitope of the α3 chain of collagen type VI with an immunological binding partner as described above, and determining the amount of binding of said immunological binding partner.

Preferably said C-terminal epitope is comprised in a C-terminal amino acid sequence . . . KPGVISVMGT-COOH (SEQ ID. NO:1).

Said method may be used to quantify the amount of said C-terminal epitope of the α3 chain of collagen type VI in a biofluid.

Said biofluid may be for instance serum, plasma, urine or amniotic fluid.

Said immunoassay may be a competition assay or a sandwich assay such as a radioimmunoassay or an enzyme-linked immunosorbent assay (ELISA).

Such a method may further comprise correlating the quantity of said C-terminal epitope of the α3 chain of collagen type VI determined by said method with standard normal values of said C-terminal epitope of the α3 chain of collagen type VI to evaluate a change thereof from normal levels.

The invention includes a method of investigating the rate of formation of extracellular matrix comprising conducting an assay by a method as described above to obtain a measure of the level in a biofluid sample of collagen type VI α3 fragments comprising an epitope comprised in a C-terminal amino acid sequence . . . KPGVISVMGT-COOH (SEQ ID. NO:1).

Such a method may further comprise forming an index comparing the said measured level of collagen type VI α3 fragments with a measured level in the same sample of a biomarker of the degradation of collagen type VI. Such a biomarker of degradation may be a fragment of MMP degraded collagen type VI. Such an assay may be based on antibody reactivity to the N-terminal sequence YRG-PEGPQGP . . . (SEQ ID No: 13) as described in Veidal 2011 and in WO2010/115749.

We have now investigated the modulation of serological collagen peptide biomarkers in response to long-term unloading in the form of bed rest and subsequent reloading and we have similarly studied these biomarkers in COPD exacerbation events.

In the bed rest investigation, subjects were immobilized through bed rest with or without a vibration device countermeasure for 8 weeks followed by remobilization through habitual physical activity. Both groups lost muscle mass and strength during the immobilization, with slightly more lost in the control group than in the rested group. Both groups regained muscle mass and strength during remobilization.

During immobilization, biomarkers of collagen type III pro-peptide (PRO-C3) and the collagen type VI biomarker of the invention (PRO-C6) display somewhat similar temporal patterns. While that of the invention initially drops slightly following the onset of immobilization, both PRO-C3 and PRO-C6 eventually increase with immobilization over time. At the onset of remobilization, a slight initial drop can again be observed followed by an increase that on the part of PRO-C6 was bigger in the CTRL than in the RVE group, followed by a return to baseline in both biomarkers.

The C6M biomarker is essentially unresponsive to bed rest unloading, but spikes briefly in response to reloading, with no significant difference between groups.

PRO-C6 can therefore be seen to be a biomarker of remodelling associated with changes in physical activity and changes in LBM (lean body mass). Low PRO-C6 at baseline is associated with a phenotype that is more prone to changes in LBM, both gain and loss. Thus, an assay for this sequence may be used to identify amongst individuals subjected to involuntary immobilization, e.g. from hospitalization, those who are at increased risk of muscle loss and thus qualify treatment decisions to counter LBM loss.

Furthermore, the assay may be used to monitor the rate of connective tissue remodeling, particularly muscle turnover, and to give information on the effectiveness of candidate treatments for modulating that rate.

This biomarker may be used to assist in the diagnosis of COPD exacerbation events, or to provide prognosis as to which patients are likely to suffer more rapid deterioration of their condition, which may make them more relevant patients to take into a clinical trial.

This biomarker may also be used to predict a response to insulin sensitizers, such as the class of compounds thiazolidinediones (e.g. balaglitazone or pioglitazone). This permits identification and monitoring of patients who will respond optimally to an insulin sensitizer, which improves the benefit to risk ratio of PPARγ agonists in the treatment of type 2 diabetes and/or non-alcoholic steatohepatitis (NASH). In this regard, the invention also provides a method for identifying a subject suitable for treatment with an insulin sensitizer, the method comprising the steps of:
  i) quantifying the amount of a C-terminal epitope of the C5 domain of the α3 chain of collagen type VI in a biofluid obtained from a subject using the Pro-C6 assay method of the invention; and
  ii) correlating an elevated value determined by step i) with a subject that is suitable for treatment with an insulin sensitizer.

A further aspect of the invention provides an assay kit for determining the quantity of a C-terminal epitope of the C5 domain of the α3 chain of collagen Type VI, preferably one comprised in a C-terminal amino acid sequence . . . KPGVISVMGT-COOH (SEQ ID. NO:1) in a biological sample, comprising an immunological binding partner of the invention and at least one of:
  a streptavidin coated 96 well plate
  a peptide which is reactive with said antibody, which may be a biotinylated peptide Biotin-L-KPGVISVMGT-COOH (SEQ ID. NO:4), wherein L is an optional linker
  an optionally biotinylated secondary antibody for use in a sandwich immunoassay
  a calibrator peptide comprising the C-terminal sequence . . . KPGVISVMGT-COOH (SEQ ID. NO:1)
  an antibody HRP labeling kit
  an antibody radiolabeling kit
  an assay visualization kit.

The term 'immunological binding partner' as used herein includes polyclonal and monoclonal antibodies and also specific binding fragments of antibodies such as Fab or F(ab')2. Thus, said immunological binding partner may be a monoclonal antibody or a fragment of a monoclonal antibody having specific binding affinity.

FIGURES

FIG. 1 shows results from a peptide specificity test of a monoclonal antibody 10A3 as the OD signal generated by serial 2-fold dilutions of standard peptide, elongated peptide and truncated peptide. STD peptide=KPGVISVMGT (SEQ ID. NO:1), elongated peptide=KPGVISVMGTA and truncated peptide=KPGVISVMG. Due to the nature of the ELISA, a lower OD corresponds to a stronger reactivity.

FIGS. 2A-2B show results from a test of the reactivity of monoclonal antibody 10A3 with human serum and amniotic fluid. FIG. 2A shows antibody binding as OD measured in a competitive ELISA was partly inhibited by human serum and human amniotic fluid. FIG. 2B shows a Western blot showing the specific bands in human serum (lane 1, 2) and amniotic fluid (lane 3, 4) and that the bands can be blocked in the presence of standard peptide (lane 6-9).

Figure 8A:
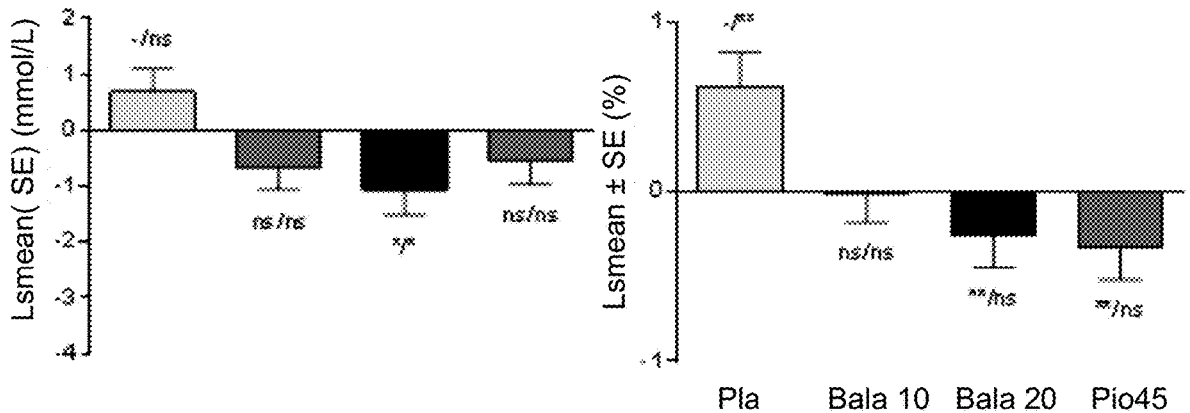
Figure 8B:
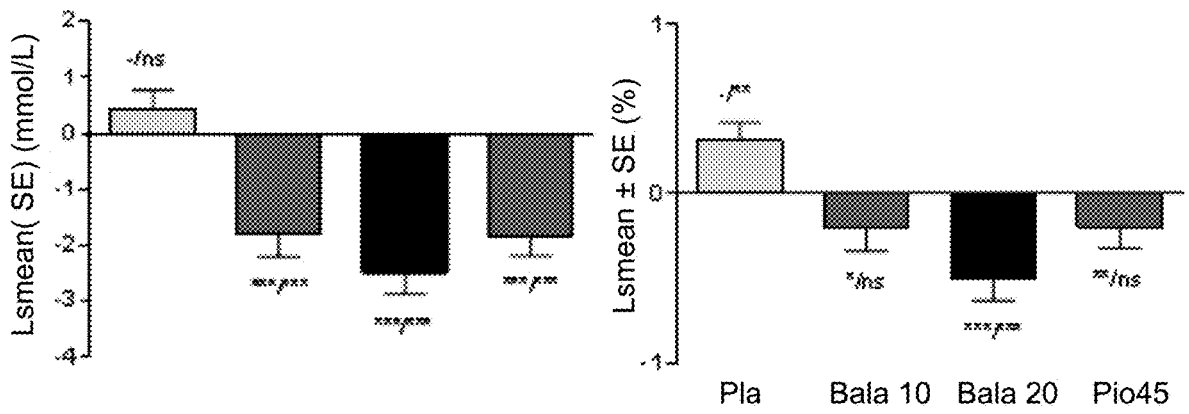
Figure 8C:
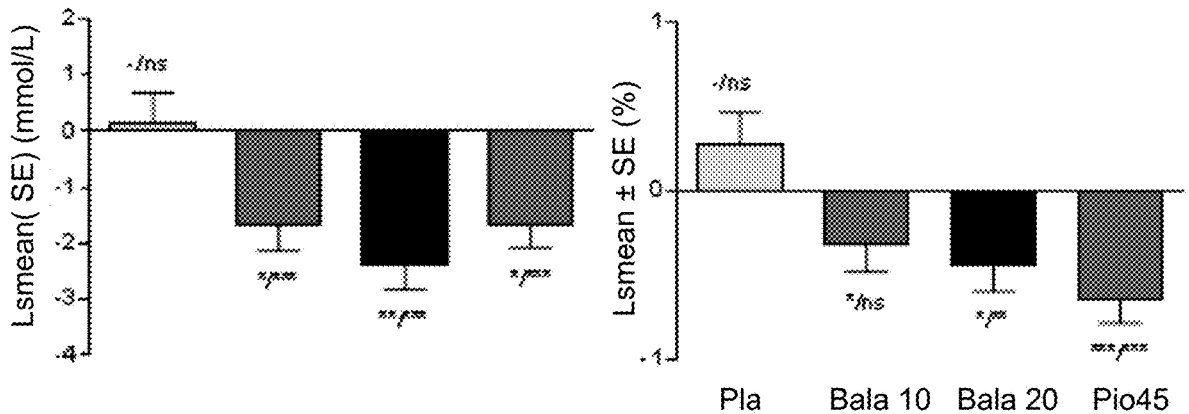

FIGS. 8A-8C show mean absolute change in fasting serum glucose (left) and blood HbA1c (right) in subgroups baseline endotrophin <6.3 ng/mL (FIG. 8A), 6.3 to 7.7 ng/mL (FIG. 8B) and >7.7 ng/mL (FIG. 8C) during the 26-week treatment period relative to baseline Pro-C6. Dunnett-adjusted level of significance of treatment against placebo before (X/') and at the end of ('/X) the 26 week treatment period. na: not applicable; ns: non-significant; *: p<0.05; : p<0.01; *: p<0.001.

Figure 9:
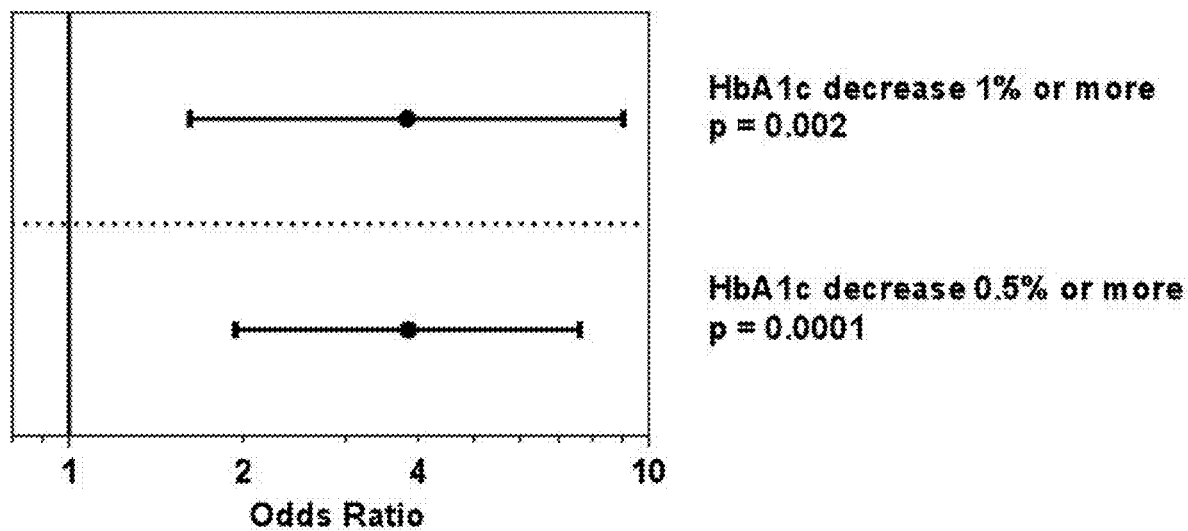

FIG. 9 shows odds ratio for responders at week 26 in the upper two endotrophin tertiles (>7.7 ng/mL) versus the lower tertile (≤7.7 ng/mL). Odds ratio for a clinically significant change of 1% (3.83, 95% CI (1.62; 9.04), p<0.002), or of 0.5% in HBA1c (3.85, 95% CI (1.94; 7.61), p<0.0001).

Figure 10A:
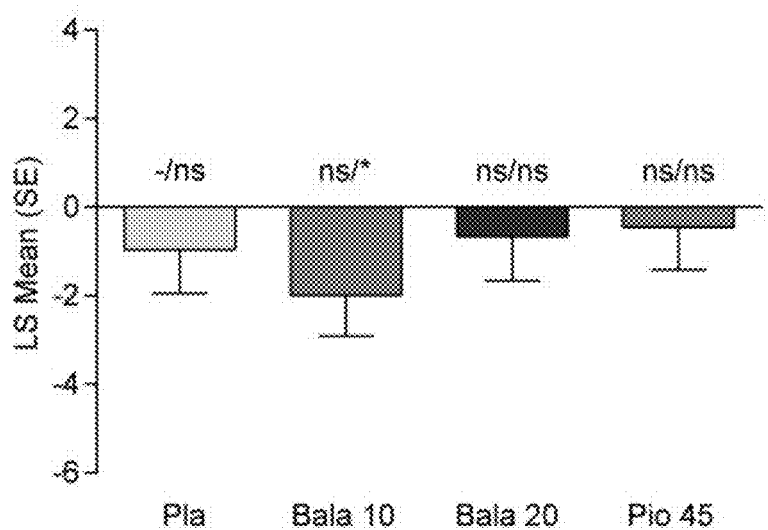
Figure 10B:
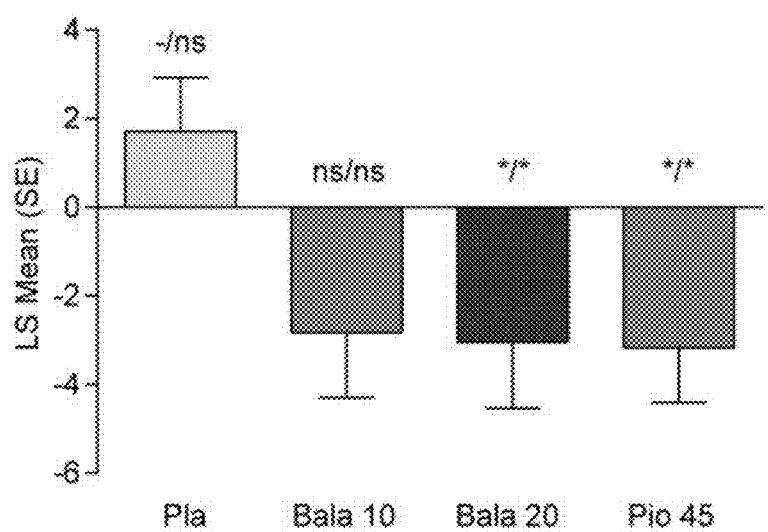
Figure 10C:
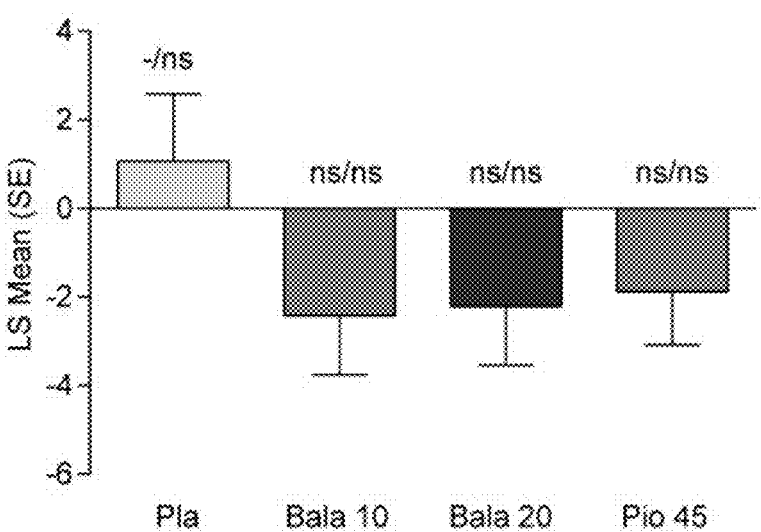

FIGS. 10A-10C show mean absolute change in HOMA-IR in subgroups baseline endotrophin <6.3 ng/mL (FIG. 10A), 6.3 to 7.7 ng/mL (FIG. 10B) and >7.7 ng/mL (FIG. 10C) during the 26-week treatment period. Dunnett-adjusted level of significance of treatment against placebo before (X/') and at the end of ('/X) the 26 week treatment period. na: not applicable; ns: non-significant; *: p<0.05; : p<0.01; *: p<0.001.

Figure 11A:
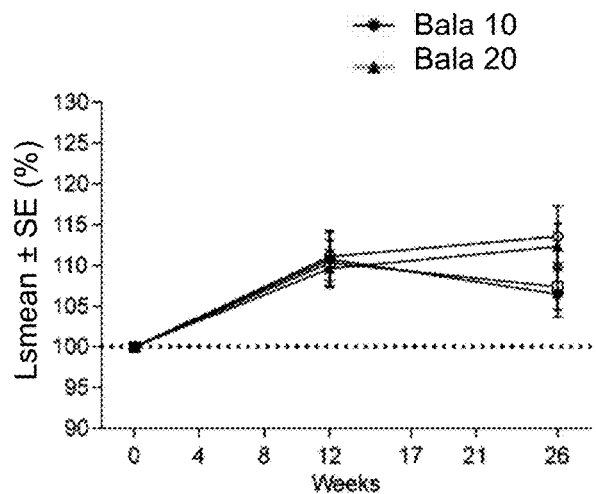
Figure 11D:
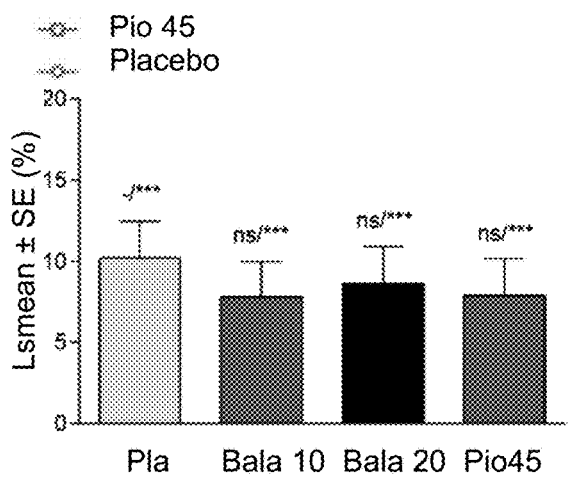
Figure 11B:
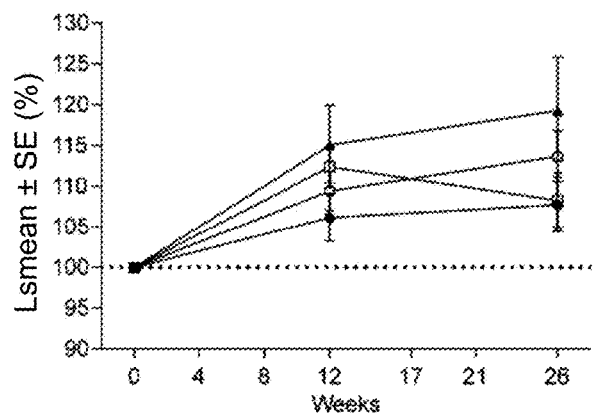
Figure 11E:
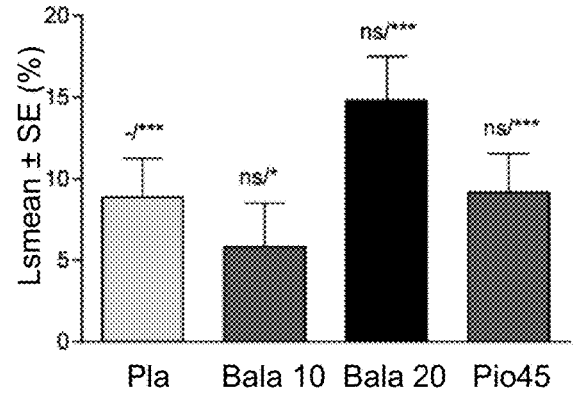
Figure 11C:
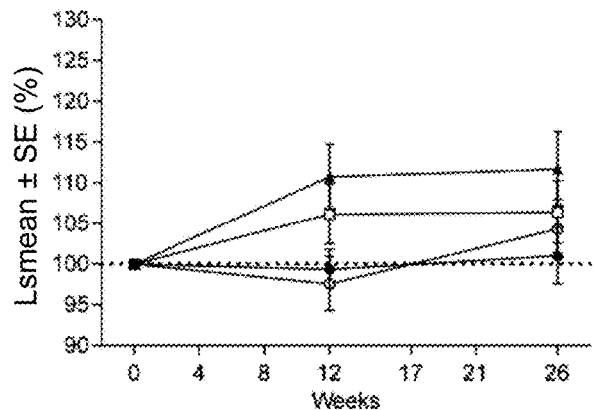

FIG. 11A-11C show the effect of treatment on serum Pro-C6 levels. Serum Pro-C6 is expressed as percent change relative to baseline until end of treatment (week 26) according to tertiles subgroups of baseline endotrophin <6.3 ng/mL (FIG. 11A), 6.3 to 7.7 ng/mL (FIG. 11B) and >7.7 ng/mL (FIG. 11C) Pro-C6. Figures show the least squares estimates (±standard error).

Figure 11F:
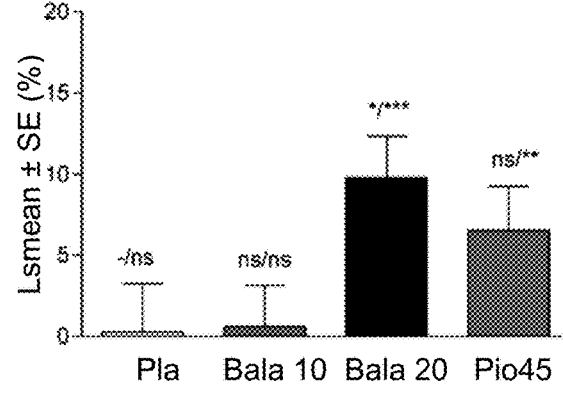

FIGS. 11D-11F show the mean change in Pro-C6 relative to subgroups baseline endotrophin <6.3 ng/mL (FIG. 11D), 6.3 to 7.7 ng/mL (FIG. 11E) and >7.7 ng/mL (FIG. 11F) using Dunnett-adjusted level of significance of treatment against placebo before (X/') and at the end of ('/X) the 26 week treatment period. na: not applicable; ns: non-significant; *: p<0.05; : p<0.01; *: p<0.001.

Figure 12A:
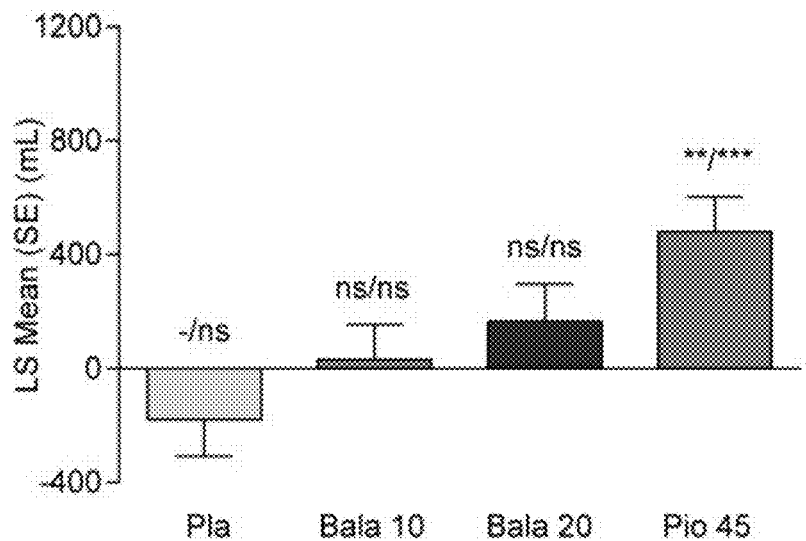
Figure 12B:
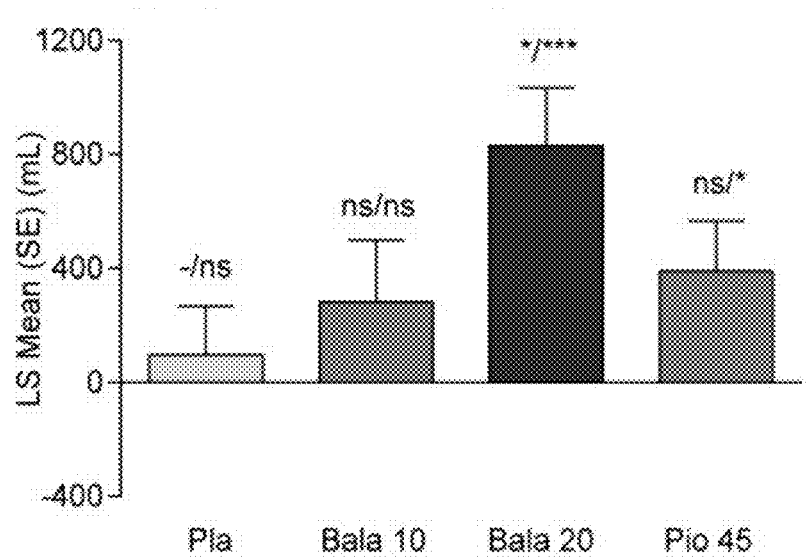
Figure 12C:
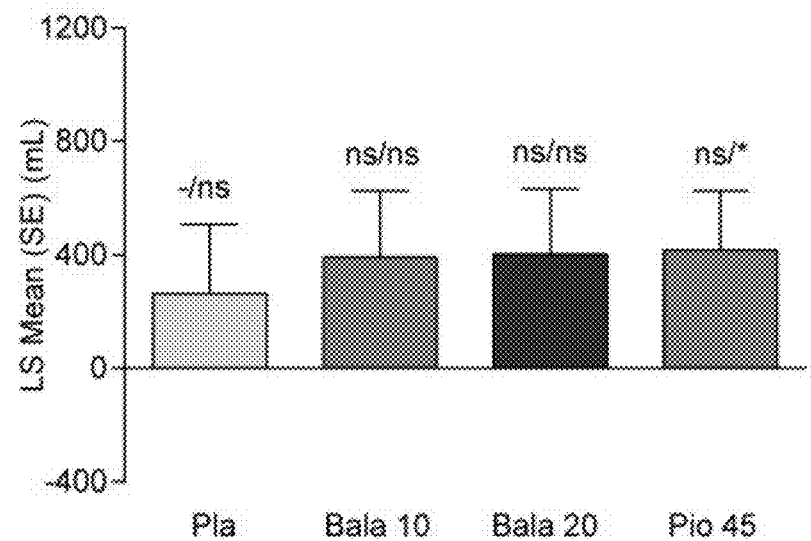

FIGS. 12A-12C show the mean absolute change in lower leg volume in subgroups baseline endotrophin <6.3 ng/mL (FIG. 12A), 6.3 to 7.7 ng/mL (FIG. 12B) and >7.7 ng/mL (FIG. 12C) during the 26-week treatment period. Dunnett-adjusted level of significance of treatment against placebo before (X/') and at the end of ('/X) the 26 week treatment period. na: not applicable; ns: non-significant; *: p<0.05; : p<0.01; *: p<0.001.

EXAMPLES

Example 1: Antibody Development for Pro-C6

We used the last 10 amino acids of the type VI collagen α3 chain ($^{3168}$'KPGVISVMGT'$^{3177}$ (SEQ ID. NO:1)) as an immunogenic peptide to generate specific epitope monoclonal antibodies. The methods used for monoclonal antibody development were as previously described (Barascuk).

Briefly, 4-6-week-old Balb/C mice were immunized subcutaneously with 200 µl emulsified antigen with 60 µg of the immunogenic peptide. Consecutive immunizations were performed at 2-week intervals in Freund's incomplete adjuvant, until stable sera titer levels were reached, and the mice were bled from the 2nd immunization on. At each bleeding, the serum titer was detected and the mouse with highest antiserum titer and the best native reactivity was selected for fusion. The selected mouse was rested for 1 month followed by intravenous boosting with 50 µg of immunogenic peptide in 100 µl 0.9% sodium chloride solution 3 days before isolation of the spleen for cell fusion.

The fusion procedure has been described elsewhere (Gefter). Briefly, mouse spleen cells were fused with SP2/0 myeloma fusion partner cells. The fusion cells were raised in 96-well plates and incubated in the CO2-incubator. Here standard limited dilution was used to promote monoclonal growth. Cell lines specific to the selection peptide and without cross-reactivity to neither elongated peptide (KPGVISVMGTA (SEQ ID. NO:2), Chinese Peptide Company, China) nor truncated peptide (KPGVISVMG (SEQ ID. NO:3), American Peptide Company, USA) were selected and sub-cloned. At last the antibodies were purified using an IgG column.

The antibodies generated were sequenced and the CDRs determined.

The sequence of the chains are as follows (CDRs underlined and in bold):

```
Heavy Chain Sequence (mouse IgG1 isotype)
                                  (SEQ ID. NO: 5)
EVQLQQSGPVMVKPGTSVKTSCKASGYTFT DFNMN WVKQSHGKSLEWIGA

INPHNGATSYNQKFSG KATLTVDKSSSTAYMELNSLTSDDSAVYYCAR WG

NGKNS WGQGTTLTVSSAKTTPPSVYPLAPGSAAQTNSMVTLGCLVKGYFP

EPVTVTWNSGSLSSGVHTFPAVLQSDLYTLSSSVTVPSSTWPSETVTCNV

AHPASSTKVDKKIVPRDCGCKPCICTVPEVSSVFIFPPKPKDVLTITLTP

KVTCVVVDISKDDPEVQFSWFVDDVEVHTAQTQPREEQFNSTFRSVSELP

IMHQDWLNGKEFKCRVNSAAFPAPIEKTISKTKGRPKAPQVYTIPPPKEQ

MAKDKVSLTCMITDFFPEDITVEWQWNGQPAENYKNTQPIMDTDGSYFVY

SKLNVQKSNWEAGNTFTCSVLHEGLHNHHTEKSLSHSPGK

CDR-H1:
                                  (SEQ ID. NO: 6)
DFNMN

CDR-H2:
                                  (SEQ ID. NO: 7)
AINPHNGATSYNQKFSG

CDR-H3:
                                  (SEQ ID. NO: 8)
WGNGKNS

Light Chain Sequence (mouse Kappa isotype)
                                  (SEQ ID. NO: 9)
DVVMTQTPLSLPVNLGDQASISC RSSQRIVHSNGITFLE WYLQKPGQSPK

LLIY RVSNRFS GVPDRFSGSGSGTDFTLKISRVEAEDLGLYYC FQGSHVP

LT FGAGTRLELKRADAAPTVSIFPPSSEQLTSGGASVVCFLNNFYPKDIN

VKWKIDGSERQNGVLNSVVTDQDSKDSTYSMSSTLTLTKDEYERHNSYTC

EATHKTSTSPIVKSFNRNEC

CDR-L1:
                                  (SEQ ID. NO: 10)
RSSQRIVHSNGITFLE

CDR-L2:
                                  (SEQ ID. NO: 11)
RVSNRFS

CDR-L3:
                                  (SEQ ID. NO: 12)
FQGSHVPLT
```

Pro-C6 Assay Protocol:

ELISA-plates used for the assay development were Streptavidin-coated from Roche (cat.: 11940279). All ELISA plates were analyzed with the ELISA reader from Molecular Devices, SpectraMax M, (CA, USA). We labeled the selected monoclonal antibody with horseradish peroxidase (HRP) using the Lightning link HRP labeling kit according to the instructions of the manufacturer (Innovabioscience, Babraham, Cambridge, UK). A 96-well streptavidin plate was coated with biotinylated synthetic peptide biotin-KPGVISVMGT (SEQ ID. NO:4) (Chinese Peptide Company, China) dissolved in coating buffer (40 mM $Na_2HPO_4$, 7 mM $KH_2PO_4$, 137 mM NaCl, 2.7 mM KCl, 0.1% Tween 20, 1% BSA, pH 7.4) and incubated 30 minutes at 20° C. 20 µL of standard peptide or samples diluted in incubation buffer (40 mM $Na_2HPO_4$, 7 mM $KH_2PO_4$, 137 mM NaCl, 2.7 mM KCl, 0.1% Tween 20, 1% BSA, 5% Liquid II, pH 7.4) were added to appropriate wells, followed by 100 µL of HRP conjugated monoclonal antibody 10A3, and incubated 21 hour at 4° C. Finally, 100 µL tetramethylbenzinidine (TMB) (Kem-En-Tec cat. 438OH) was added and the plate was incubated 15 minutes at 20° C. in the dark. All the above incubation steps included shaking at 300 rpm. After each incubation step the plate was washed five times in washing buffer (20 mM Tris, 50 mM NaCl). The TMB reaction was stopped by adding 100 µL of stopping solution (1% $H_2SO_4$) and measured at 450 nm with 650 nm as the reference.

Pro-C6 Technical Evaluation:

The lowest limit of detection (LLOD) was determined from 21 zero samples (i.e. buffer) and calculated as the mean+3× standard deviation. The intra-assay variation and inter-assay variations were determined by 12 independent runs of 8 QC samples with each run consisting of double determinations of the samples. Dilution recovery was determined in 4 serum samples and 4 heparin plasma samples and was calculated as a percentage of recovery of diluted samples from the 100% sample.

Example 2: PRO-C6 in Muscle Loss Studies

Measurement of Pro-C3, C6M Assays in Berlin Bed Rest Study:

The level of C-terminal of α3 chain is expected to reflect the level of newly formed mature type VI collagen. In order to investigate the synthesis of type VI collagen, we developed the Pro-C6 ELISA kit described above targeting the C-terminal of α3 chain. In addition, type VI collagen is also a substrate of MMPs (Veidal 2011). Previous studies showed that both MMP-2 and MMP-9 are relevant to muscle atrophy (Reznick 2003 and Giannelli 2005). Therefore, type VI collagen degradation fragments generated by MMP-2 and MMP-9 are of interest in such a process.

In this study, we measured three biomarkers Pro-C6 (measuring the C-terminal α3(VI) chain) and C6M (measuring type VI collagen fragment degraded by MMP-2 and MMP-9)(Veidal 2011), and Pro-C3 (measuring the true synthesis of type III collagen) (Nielsen), which directly measure the turnover of type III and VI collagen in the Berlin bed rest study—using bed rest immobilization and remobilization as a human model of muscle atrophy and hypertrophy.

The Berlin bed rest study has been described elsewhere (Rittweger 2006 and Belavy 2009). Briefly, 20 healthy young men were recruited and underwent a strict 8-week bed rest study. The 20 young men were then randomly divided into two groups. The resistive vibration exercise group (RVE) group was assigned to resistive vibration exercise 11 times per week. The resistive vibration exercises were performed by a vibration exercise apparatus at the end of the beds and pulling the subject towards the vibration plate with waist and shoulder straps and handles for the subjects to pull themselves towards the plate. The control group (CTRL) was not allowed to perform any exercise during the 8-week bed rest. Serum samples were obtained 2 days before the study (BDC-2), in the bed rest period (BR+) and in the following recovery period (R+). The serum samples were stored at −80° C. until further measurement. The muscle mass of both groups were assessed by MRI and DXA during the three periods.

The protocols of Pro-C3 and C6M assays have been described elsewhere (Nielsen 2013 and Kuo 1997). The Pro-C3 assay measures levels of a pro-peptide fragment of collagen type III. The C6M assay measures MMP degradation fragments of mature collagen type VI. Briefly, in Pro-C3 assay, a 96-well streptavidin plate was coated with biotinylated synthetic peptide and incubated 30 minutes at 20° C. 20 μL of standard peptide or 1:2 diluted serum samples were added to appropriate wells, followed by 100 μL of HRP conjugated monoclonal antibody NB61N-62, and incubated 20 hour at 4° C. Finally, 100 μL TMB was added and the plate was incubated 15 minutes at 20° C. in the dark. The TMB reaction was stopped by adding 100 μL of stopping solution (1% $H_2SO_4$) and measured at 450 nm with 650 nm as the reference. In C6M assay, biotinylated synthetic peptide is coated to a 96-well streptavidin plate. 20 μL of standard peptide or 1:2 diluted serum samples are added, followed by 100 μL of HRP conjugated monoclonal antibody, and incubated 1 hour at 20° C. The plate was read after the development by TMB.

Figure 1:
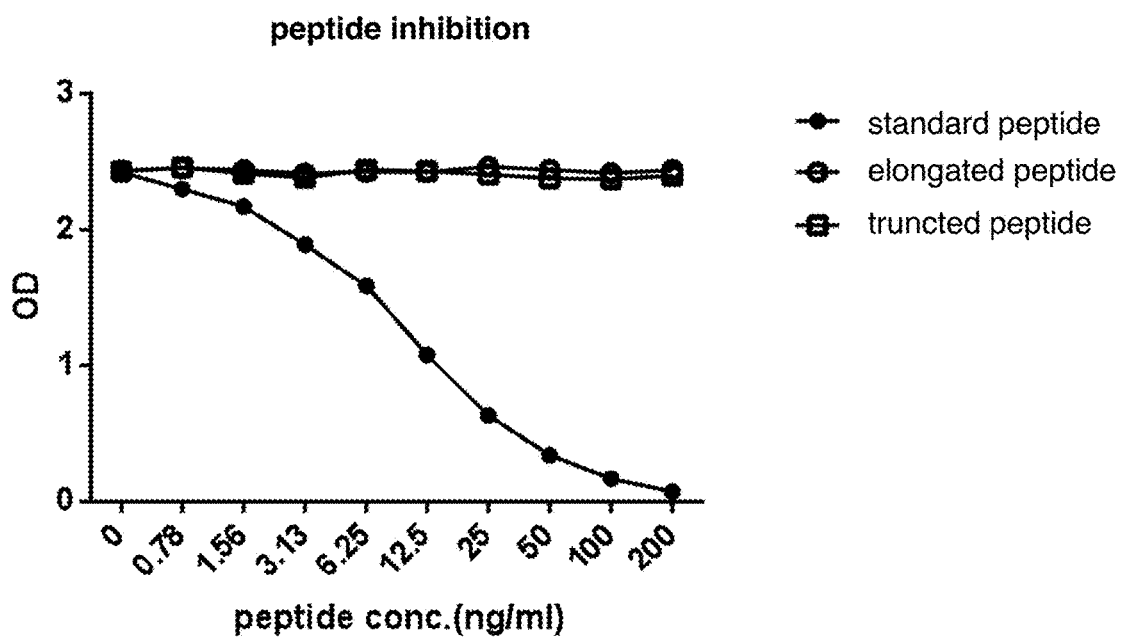
Figure 2A:
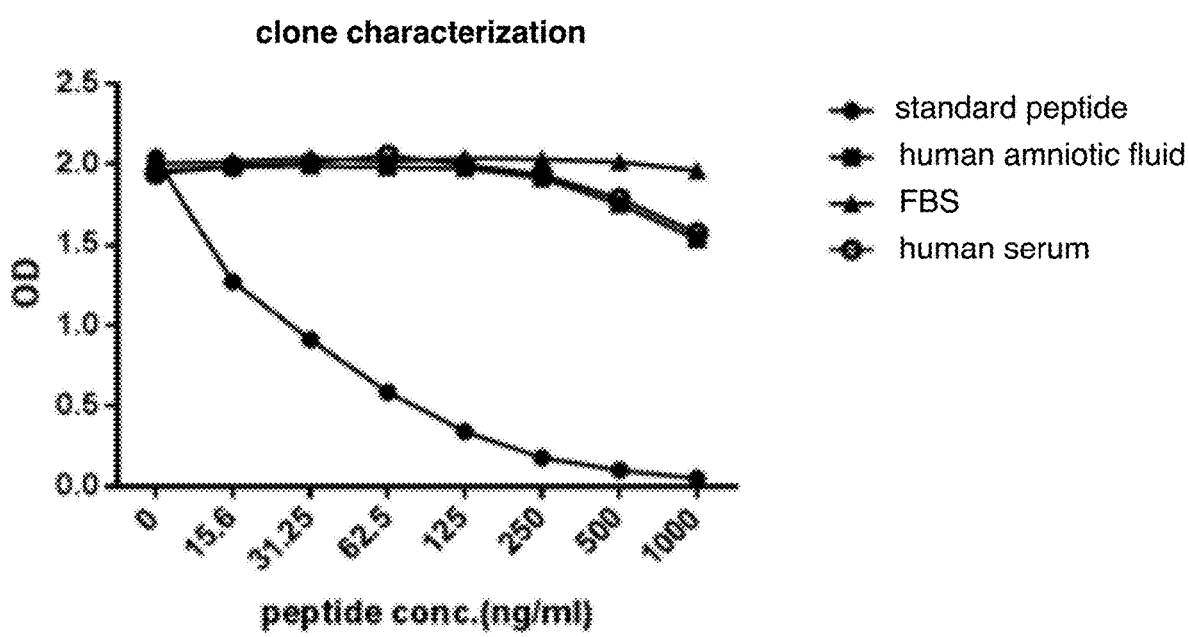
Figure 2B:
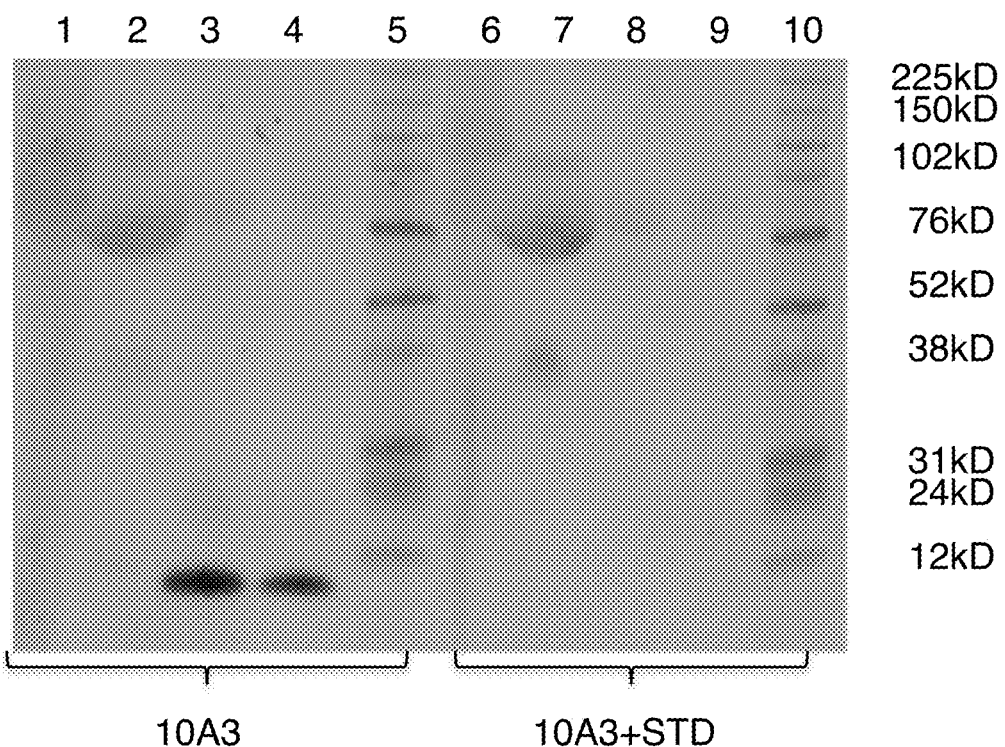

Results:

The chosen antibody 10A3 specifically recognized the last 10 amino acids of C-terminal COL6A3 3168'KPGVISVMGT'3177 (SEQ ID. NO:1), but did not recognize elongated peptide KPGVISVMGTA nor truncated peptide KPGVISVMG (FIG. 1). Native reactivity of the chosen antibody was assessed using human serum pool and human amniotic fluid pool. In competitive ELISA, the signals were partly inhibited by both serum and amniotic fluid (FIG. 2A). The results were confirmed by western blot that the antibody recognized around 10 kD bands, while the signal was completely blocked in the presence of the standard peptide (FIG. 2 B).

Figure 3:
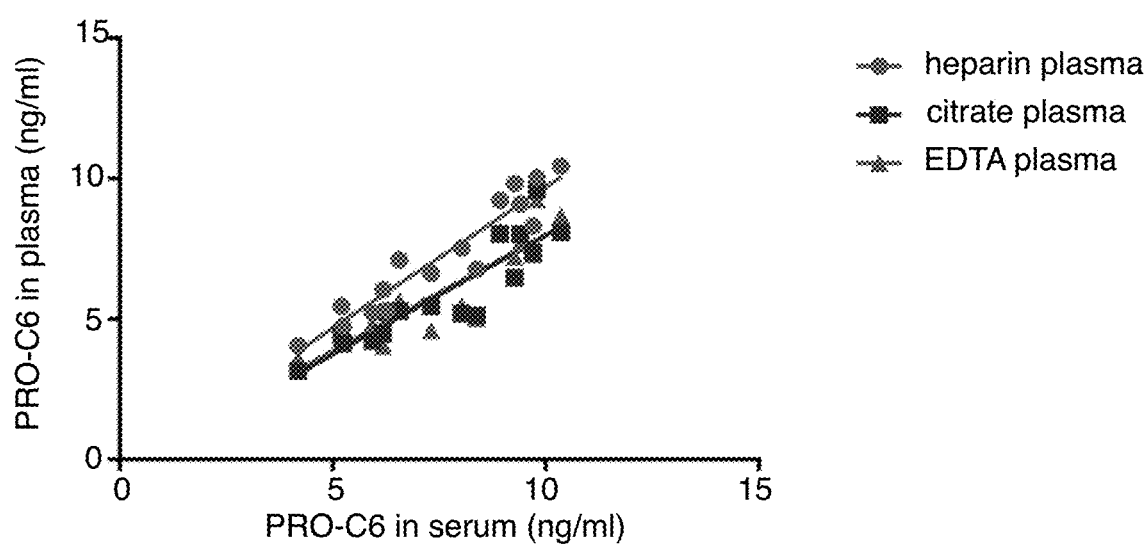
FIG. 3 shows results from linear regression analysis of Pro-C6 levels measured on three different kinds of plasma vs serum, showing strong correlations between serum levels and each kind of plasma (P<0.0001).

The measurement range of Pro-C6 competitive ELISA was determined by LLOD and ULOD, providing the range from 0.15 ng/ml to 58.39 ng/ml. The inter- and intra-assay variability is 15.2% and 4.8%, respectively. The dilution recovery in human serum and heparin plasma were both within 100±20% (Table 1). The correlation between human serum and each of heparin plasma, citrate plasma and EDTA plasma was relatively high (FIG. 3, $p<0.0001$), which showed the Pro-C6 levels were constant despite the different blood preparation methods.

TABLE 1

Table depicting dilution recovery.

| Serum samples | Dilution recovery | Heparin plasma samples | Dilution recovery |
| --- | --- | --- | --- |
| undiluted | 100 | undiluted | 100 |
| dilution 1:2 | 91 | dilution 1:2 | 105 |
| dilution 1:4 | 91 | dilution 1:4 | 100 |
| dilution 1:8 | 80 | dilution 1:8 | 109 |

Samples were diluted in serial 2-fold dilution steps concentration was measured in these serial dilutions. Dilution recovery was obtained by multiplying measured concentrations with the dilution factor and expressed as percent of the concentration of the undiluted (starting) sample. The table shows that the signal dilutes linearly and stays within +/−20% within and 8-fold dilution range.

Figure 4A:
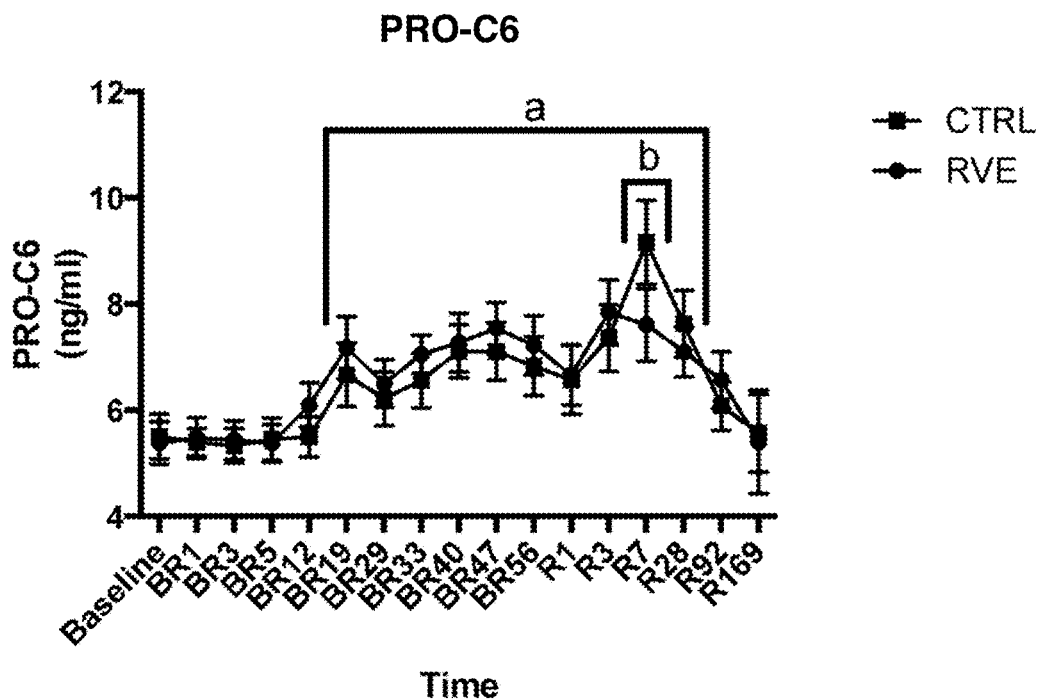
FIGS. 4A-4C show PRO-C3, PRO-C6 and C6M levels over time in a bed rest and remobilisation (BBR) study.
Figure 4B:
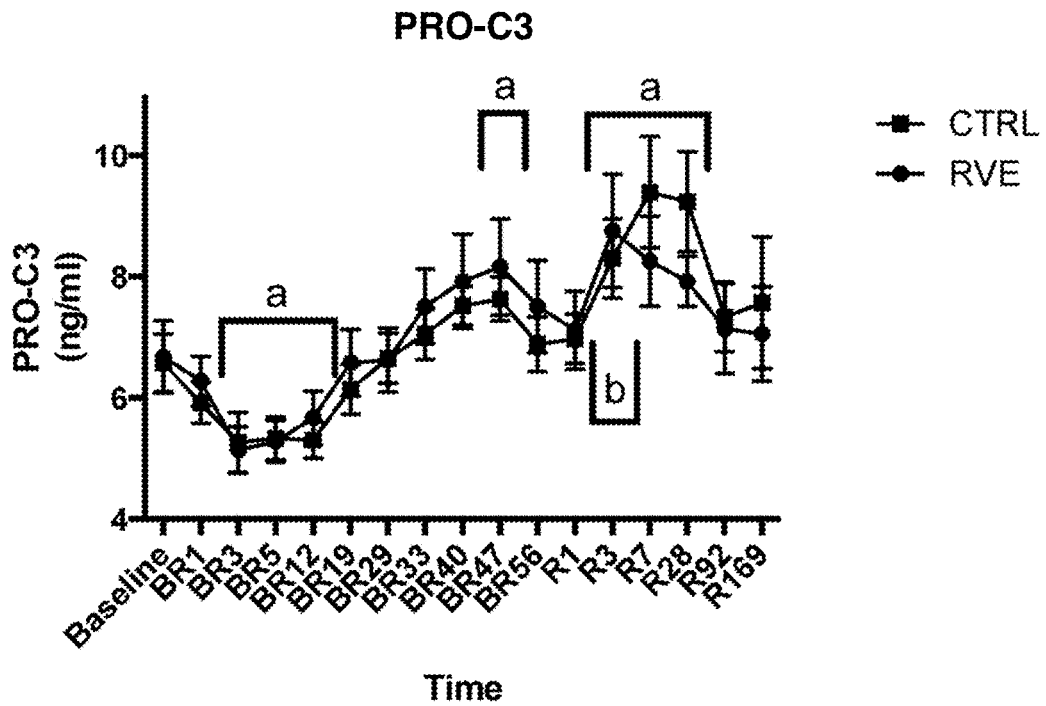
Figure 4C:
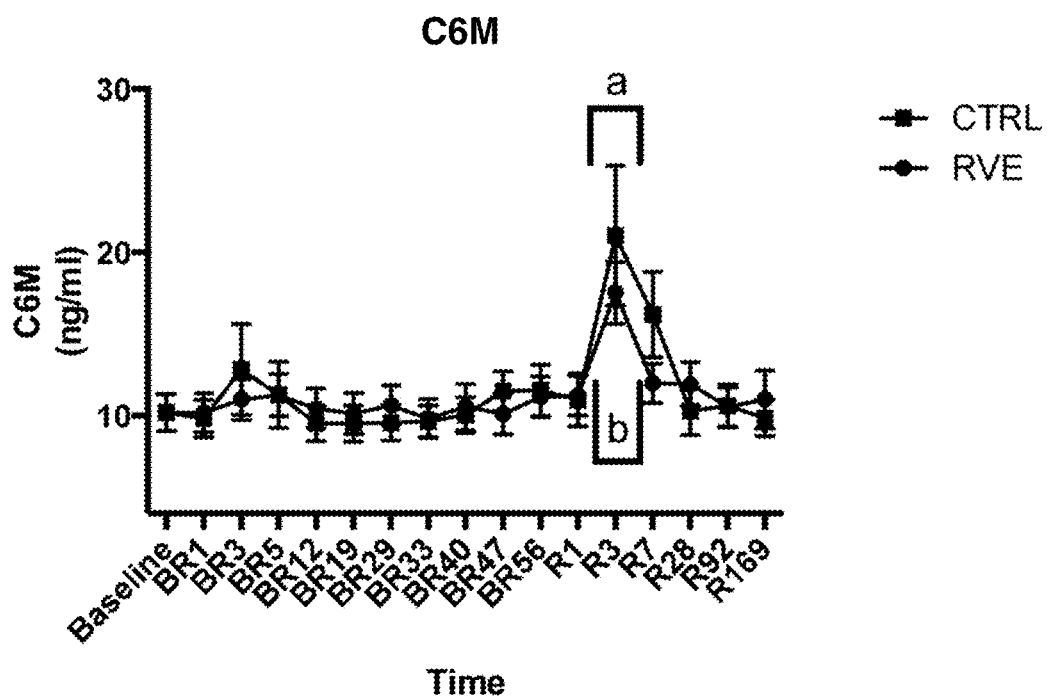

Biomarker Profiles in Berlin Bed Rest Study:

The levels of the three biomarkers referred to above measured in the Berlin Bed rest study (BBR) are seen in FIGS. 4A-4C. "BR" time points denote bed rest immobilization time points and "R" time points denote remobilization time points. The number suffix denotes the number of days into the bed rest or remobilization period. "a" denotes significant difference from baseline and "b" denotes a significant difference from the last time point of the immobilization period. Data are expressed as means+/−SEMs.

As seen in FIG. 4A, PRO-C3 displayed a significant time effect in the form of an initial decrease of approximately 20% upon immobilization (being significantly different from baseline from BR3 through BR12, $p<0.004$ for all time points) followed by an increase at the end of the immobilization (BR40 being significantly different from baseline, $\rho=0.05$). Interestingly, at the onset of remobilization, a similar pattern could be observed with an initial decrease followed by an increase (with time points R3 through R28 being significantly higher than baseline, $p<0.03$ for all time points, and R3 being significantly higher than the last time point of immobilization, BR56, $\rho=0.02$). At the last two time points, 13 weeks following the onset of immobilization the biomarker levels were back to baseline. There were no significant between-group differences, nor a significant time*treatment interaction effect.

When we compared individual biomarker levels of PRO-C3 with LBM and changes therein, we found that individual levels of PRO-C3 correlated significantly with LBM at baseline ($R^2=0.2869$, $R=0.536$, $\rho=0.0149$). Furthermore, we found that the level of biomarker at its peak at BR47, correlated significantly with the amount of LBM lost during immobilization ($R^2=0.2056$, $R=0.453$, $\rho=0.0447$).

The PRO-C6 biomarker changed over time during the course of immobilization (significant time effect, $p<0.0001$) in the form of an increase after approximately one week of immobilization, reaching a peak level approximately 30% higher than baseline during the last couple of weeks of immobilization (being significantly higher than baseline from BR19 to R28, peaking at BR47, $\rho=0.0002$). There were no between-group differences during the immobilization period (no significant treatment effects or treatment*time interactions).

During re-mobilization, both time and time*treatment interaction effects manifested. This was in the form of an increase that peaked one week into remobilization (an 20% increase relative to the last day of immobilization, BR56, $\rho=0.011$), followed by a gradual return to baseline values. The interaction effect was not manifested in any post hoc tests, owing to high variation at the R7 time point.

When we compared individual biomarker levels of PRO-C6 with LBM and changes therein, we found that the level of PRO-C6 was not related to LBM at all, but positively related to change in LBM during immobilization ($R^2=0.2794$, $R=0.529$, $\rho=0.0166$) meaning that higher levels of PRO-C6 were associated with less loss of LBM. We also found that PRO-C6 was negatively related to the amount of LBM (re)gained during remobilization ($R^2=0.3365$, $R=0.580$, $\rho=0.0073$), meaning that higher levels were associated with less (re)gain of LBM during remobilization.

The C6M biomarker was essentially unaffected by immobilization (no time effect in the immobilization time period), but increased briefly 30-40% at the beginning of remobilization (a significant time effect at $p<0.0001$ during the immobilization period). There were no treatment effects during immobilization and although it may appear as if the increase in the C6M signal is bigger in the CTRL group than in the RVE group, this did not reach significance (the time*treatment interaction did not reach significance and thus no post hoc test was made). There were no differences between the groups.

When we compared individual biomarker levels of PRO-C6 with LBM and changes therein, we found that the level of PRO-C6 was not related to LBM at all, but positively related to muscle loss during immobilization ($R^2=0.2794$, $R=0.529$, $\rho=0.0166$) and negative related to the amount of muscle (re)gained during remobilization ($R^2=0.3365$, $R=0.580$, $\rho=0.0073$).

TABLE 2

Correlation matrix for biomarker vs. anthropometric variables. BioM (Biomarker), Lean Body mass (LBM), Leg Muscle Volume (LMV, from MRI), Loss is the absolute LBM change during immobilization, i.e. higher negative equals bigger loss; Gain is total LBM regain during remobilization.

|  | PRO-C3 | | PRO-C6 | | C6M | |
| --- | --- | --- | --- | --- | --- | --- |
|  | R | p | R | p | R | p |
| $BioM_{Baseline}$ vs. $LBM_{Baseline}$ | 0.536 | 0.0149* | 0.022 | 0.9270 | 0.595 | 0.0057* |
| $BioM_{BR47}$ vs. leg $LBM_{Loss}$ | 0.453 | 0.0447* | 0.529 | 0.0166* | 0.102 | 0.6684 |
| $BioM_{R3}$ vs. leg $LBM_{Gain}$ | −0.171 | 0.4705 | −0.580 | 0.0073* | −0.269 | 0.2509 |

PRO-C6 is seen to be a biomarker of remodelling associated with changes in physical activity and changes in LBM. Low PRO-C6 at baseline is associated with a phenotype that is more prone to changes in LBM, both gain and loss.

Example 3: PRO-C6 in COPD

Study Design:

Patients presenting with a hospital admission deemed by a medical consultant to be a COPD exacerbation during 2011 and 2012 were recruited within 24 hours of admission. Blood samples were collected at time of exacerbation and at recovery: a 4 week follow-up visit performed a median of 30 (IQR 28-34) days after admission. At follow-up visit, the patients underwent standard post-bronchodilator spirometry, and performed a six minute walking distance (6MWD). Patient-reported measures included assessments of dyspnoea, using the Medical Research Council (MRC) dyspnoea scale, at follow-up visit, and smoking history.

The inclusion criterion was a clinical diagnosis of acute COPD exacerbation at hospital admission made by a consultant physician. A physician diagnosis or radiological evidence of pneumonia was an exclusion criterion. The study comprised 69 patients with paired samples and with airflow obstruction (ratio of forced expiratory volume in one second (FEV1) to forced vital capacity (FVC) of <0.7) confirmed at follow-up visits.

ECM remodelling biomarkers:

Serum and heparin plasma samples were stored at −80° C. until analyzed. C3M, C4M, Pro-C3, P4NP 7S, ELM7, and EL-NE, were measured in serum, while C6M, Pro-C6, and VCANM were measured in heparin plasma. An overview of the assays used in this study to assess extracellular matrix remodelling appears in Table 3.

TABLE 3

Assay overview.

| Assay | Target | Detection range (ng/ml) | Intra- and inter-assay variation (%) | Reference level (ng/ml), mean (SD) | References |
|---|---|---|---|---|---|
| C3M | Collagen type III degraded by MMPs | 5.52-177 | 3.4 and 9.8 | 15.3 (3.8) | [28] |
| C4M | Collagen type IV degraded by MMPs | 22.8-748 | 4.2 and 18.5 | 55.4 (17.8) | [29] |
| C6M | Collagen type VI degraded by MMPs | 4.88-420 | 8.0 and 11.0 | 8.85 (5.1) | [30] |
| ELM7 | Elastin degraded by MMP-7 | 1.16-36.6 | 8.1 and 9.1 | 2.23 (0.74) | Preliminary data |
| EL-NE | Elastin degraded by neutrophil elastase | 1.76-167 | 8.6 and 12.9 | 4.09 (2.24) | Preliminary data |
| VCANM | Versican degraded by MMPs | 0.78-7.13 | 3.0 and 7.6 | 1.20 (0.23) | [31] |
| Pro-C3 | Collagen type III propeptide (N-terminal) | 5.32-96.4 | 6.5 and 12.4 | 12.3 (4.4) | [32] |
| P4NP 7S | Collagen type IV 7S domain (internal) | 32.9-3460 | 9.4 and 14.2 | 263 (91.3) | [33] |
| Pro-C6 | Collagen type VI propeptide (C-terminal) | 2.81-117 | 4.8 and 15.2 | 4.37 (0.69) | Preliminary data |

The reference level was provided by the manufacturer (Nordic Bioscience) and refers to the biomarker level of a healthy population in the relevant matrix, i.e. serum (C3M, C4M, Pro-C3, P4NP 7S, ELM7, EL-NE) or heparin plasma (C6M, Pro-C6, VCANM). SD, standard deviation; MMP, matrix metalloproteinase.

Patient demographics and clinical characteristics are summarised in Table 4. Patients were mostly men (71%) and ex-smokers (55%). They were hospitalised for a median [IQR] of 3 [2-6] days, and follow-up visit was performed at 30 [28-34] days after admission.

TABLE 4

Basic characteristics of the COPD population at follow-up visit 4 weeks after exacerbation onset.

| Variable | Patients (n = 69) |
|---|---|
| Age (years), median (IQR) | 67 (61-75) |
| Female sex, n (%) | 20 (29) |
| BMI (kg/m$^2$) | 25.7 (6.3) |
| Current smokers, n (%) | 31 (45) |
| Smoking pack years (years) | 52 (26) |
| Length of hospitalisation (days), median (IQR) | 3 (2-6) |
| FEV$_1$ (liters) | 1.19 (0.50) |
| FEV$_1$ (% of predicted) | 45.8 (16.1) |
| FVC (liters) | 2.55 (0.81) |
| FVC (% of predicted) | 77.5 (19.0) |
| FEV$_1$/FVC ratio | 0.46 (0.11) |
| 6MWD (meters) | 166 (119) |
| MRC dyspnoea score, median (IQR) | 4 (3-4) |

Variables are listed as mean (standard deviation) unless otherwise stated. IQR, interquartile range; BMI, body mass index; FEV$_1$, forced expiratory volume in one second; FVC, forced vital capacity; 6MWD, 6 minute walking distance; MRC, Medical Research Council.

Circulating levels of protein fragments released at time of exacerbation and at a clinically stable disease period at 30-days follow-up are presented in Table 5.

TABLE 5

Levels of circulating protein fragments at exacerbation and 30-days follow-up (ng/ml).

| | Exacerbation | Follow-up | P value |
|---|---|---|---|
| C3M | 29.24 [26.32-32.49] | 22.64 [20.78-24.67] | <0.0001 |
| C4M | 95.96 [85.83-107.28] | 73.30 [66.59-80.69] | <0.0001 |
| C6M | 19.78 [16.82-23.27] | 13.27 [11.56-15.23] | <0.0001 |
| ELM7 | 4.50 [3.91-5.17] | 3.79 [3.37-4.27] | <0.0001 |
| EL-NE | 7.79 [6.30-9.63] | 5.23 [4.41-6.21] | <0.0001 |
| VCANM | 1.69 [1.58-1.80] | 1.87 [1.78-1.97] | 0.0001 |
| Pro-C3 | 12.10 [10.60-13.81] | 12.79 [11.35-14.42] | 0.2549 |
| P4NP 7S | 510.99 [440.91-592.21] | 359.20 [312.28-413.17] | <0.0001 |
| Pro-C6 | 5.36 [4.81-5.99] | 6.38 [5.71-7.14] | <0.0001 |

Results are presented as geometric mean [95% confidence interval] and corresponding P values comparing circulating levels of protein fragments at time of exacerbation and follow-up.

Figure 5A:
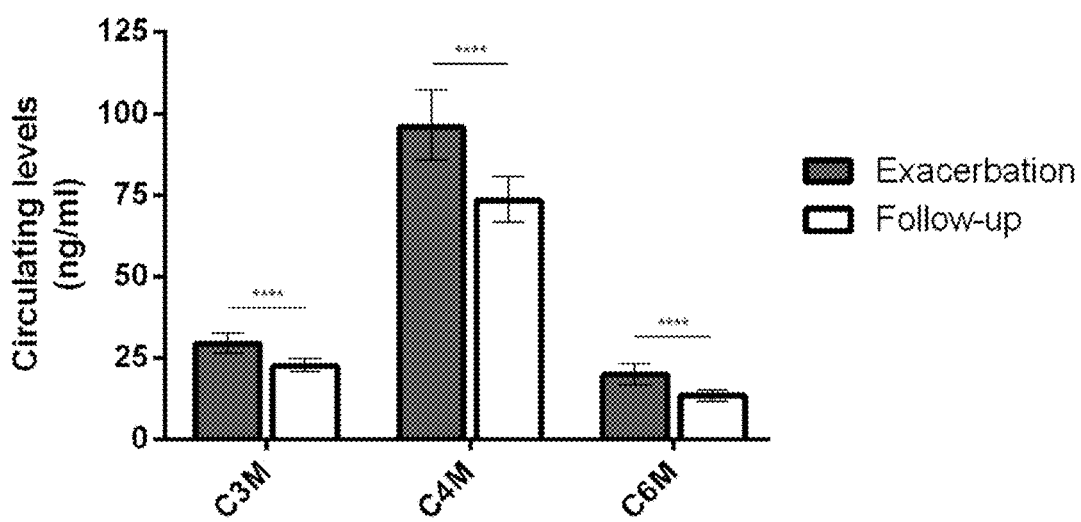
FIGS. 5A-5C show biomarker levels measured in Example 3.
Figure 5B:
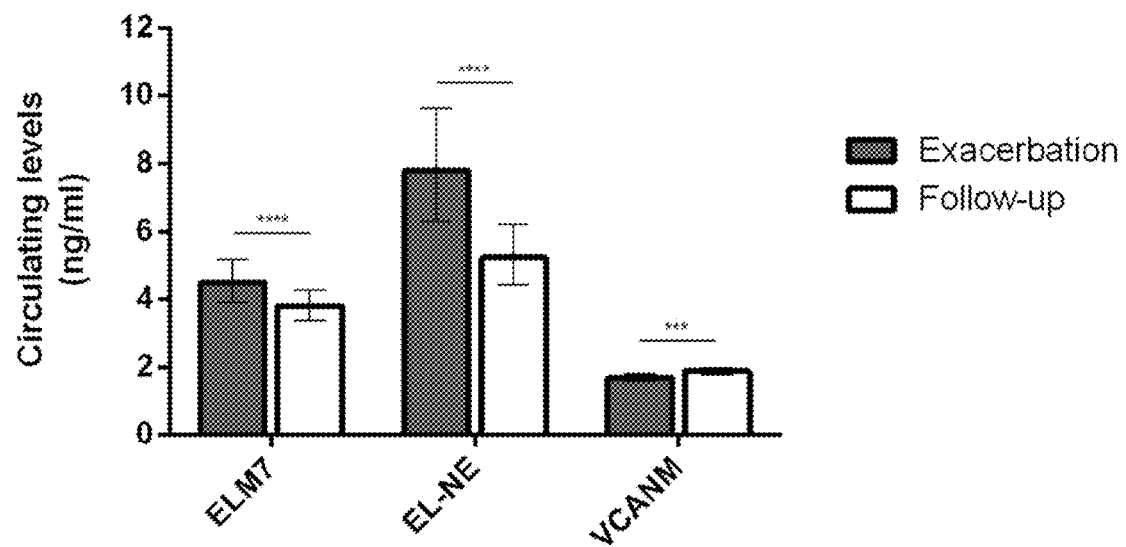
Figure 5C:
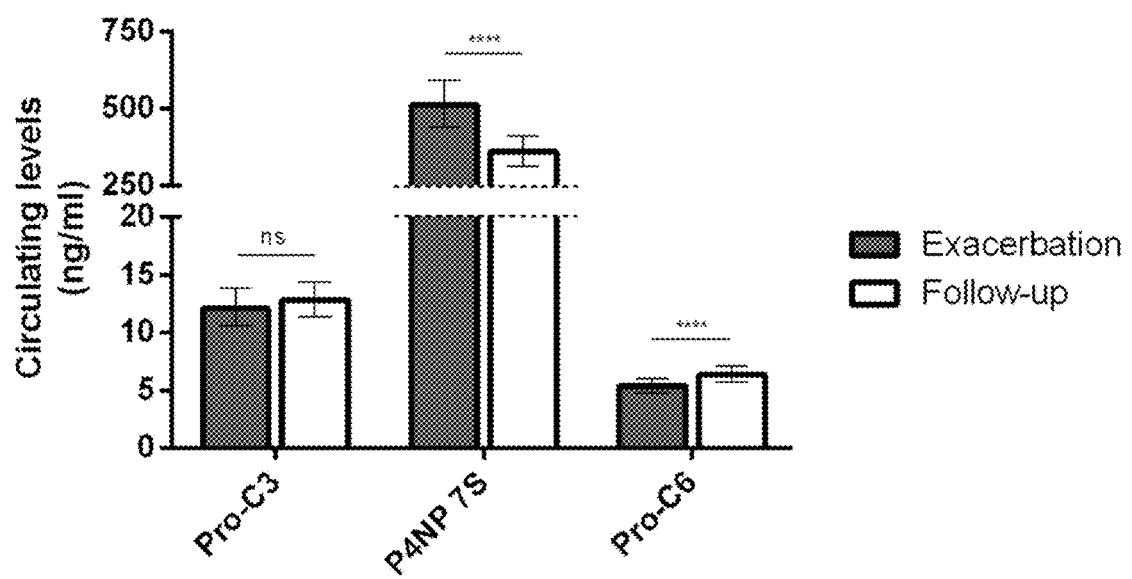

Degradation fragments of collagen type III (C3M), collagen type IV (C4M), collagen type VI (C6M), and elastin (ELM7 and EL-NE) were significantly elevated at exacerbation compared to follow-up (all P<0.0001; FIGS. 5A and 5B). In contrast, a fragment of versican degradation (VCANM) showed a significantly decreased mean level at time of exacerbation (P<0.0001; FIG. 5B). Levels of fragments related to protein formation were not significantly changed for collagen type III, but were increased for collagen type IV (P<0.0001) and decreased for collagen type VI (P<0.0001) at exacerbation compared to follow-up (FIG. 5 C). To investigate the effect of smoking on circulating levels of protein fragments, analysis was performed on current and ex-smokers, individually, with similar results (data not shown).

Figure 6A:
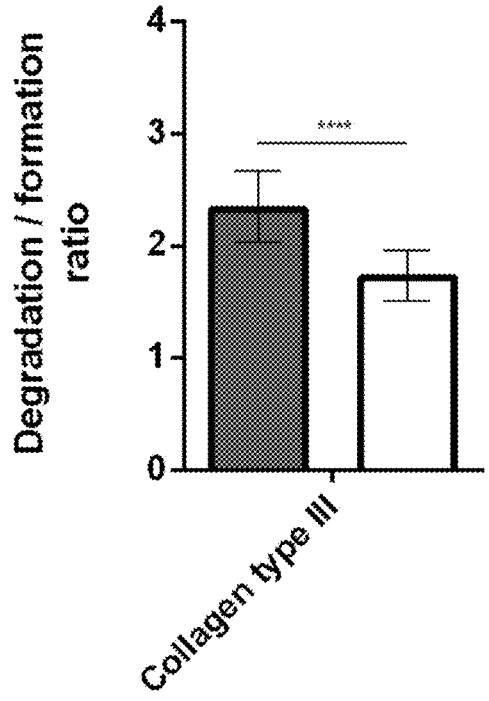
FIGS. 6A-6C show levels measured in Example 3 of ratios of degradation/formation markers of collagen type III (FIG. 6A), collagen type IV (FIG. 6B) and collagen type VI (FIG. 6C).
Figure 6B:
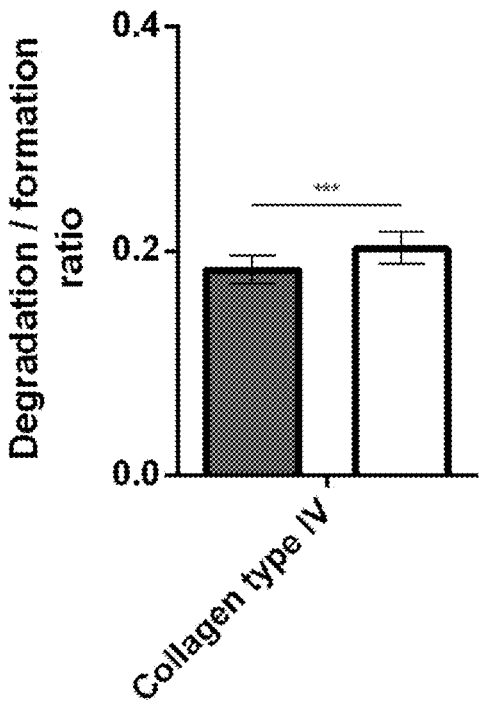
Figure 6C:
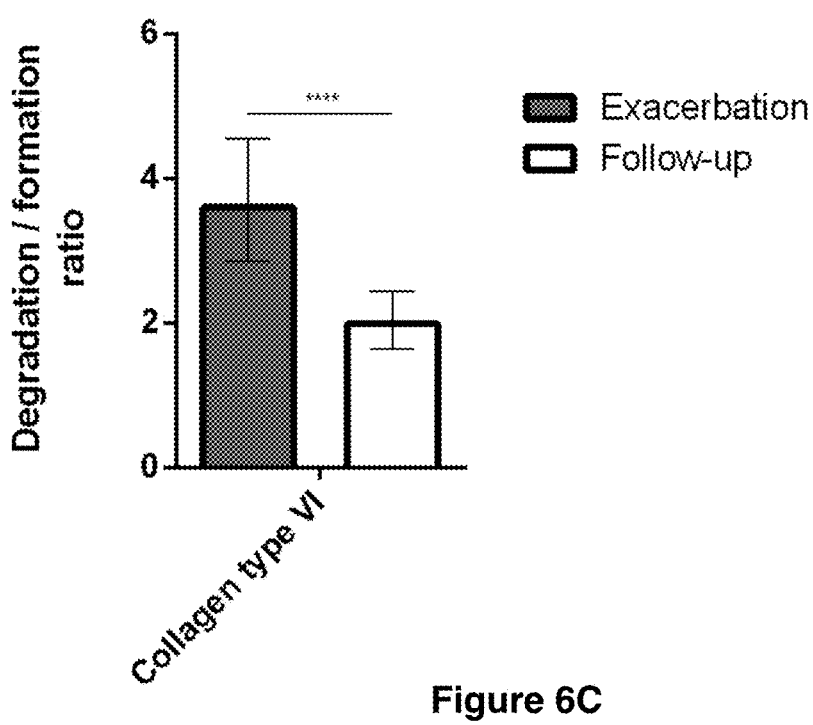

The balance between degradation and formation of collagens was investigated by calculating the ratio between fragments of degradation and formation for collagen types III, IV, and VI (FIGS. 6A-6C). The mean degradation/formation ratio [95% CI] was significantly elevated at time of exacerbation for collagen type III (2.33 [2.03-2.66] vs. 1.72 [1.51-1.96], P<0.0001) and collagen type VI (3.61 [2.86-4.56] vs. 2.00 [1.64-2.44], P<0.0001). In contrast, the collagen type IV degradation/formation ratio was 0.18 [0.17-0.20] at exacerbation and increased to 0.20 [0.19-0.22] at follow-up (P=0.0008).

At follow-up, BMI was negatively associated with C3M ($\rho=-0.271$, P=0.029), Pro-C3 ($\rho=-0.357$, P=0.010), and Pro-C6 ($\rho=-0.338$, P=0.017). Age was negatively associated with C6M ($\rho=-0.249$, P=0.039) and Pro-C6 ($\rho=-0.310$, P=0.026). No associations were seen with smoking pack years, MRC score, length of hospitalisation, sputum production, or white blood cell counts. Pro-C3 levels were positively associated with FEV1% of predicted value (% pred) and FVC % pred, and these remained significant after correcting for age, gender, BMI, smoking pack years, and smoking status (Table 4). 6MWD was negatively associated with C3M, C4M, C6M, and P4NP 7S (Table 4). Following correction for age, gender, BMI, smoking pack years, and smoking status, associations with C3M and C6M remained significant, while C4M was borderline significant and P4NP 7S was non-significant (Table 6).

TABLE 6

Associations between levels of circulating protein fragments and clinical parameters.

| | FEV1 % pred | FVC % pred | 6MWD |
|---|---|---|---|
| C3M | 0.020 | −0.182 | −0.370** (−0.311*) |
| C4M | −0.002 | −0.148 | −0.313* (−0.252£) |
| C6M | −0.012 | −0.224 | −0.354** (−0.354**) |
| ELM7 | −0.041 | −0.175 | −0.125 |
| EL-NE | −0.016 | −0.125 | −0.189 |
| VCANM | 0.021 | −0.084 | −0.096 |
| Pro-C3 | 0.391** (0.320*) | 0.312* (0.305*) | −0.009 |
| P4NP 7S | 0.042 | −0.186 | −0.278* (−0.230) |
| Pro-C6 | 0.058 | −0.013 | −0.188 |

Results are presented as Spearman correlation coefficients (ρ) for each marker. In brackets are given multivariate correlation coefficients for markers showing significant p. The multivariate linear regression analysis included age, gender, BMI, smoking pack years, and smoking status as additional explanatory variables. Significance levels: £P<0.07, *P<0.05, **P<0.01. FEV1, forced expiratory volume in one second; % pred, percentage of predicted value; FVC, forced vital capacity; 6MWD, 6 minutes walking distance.

All assays employed a monoclonal antibody directed against either a protein fragment produced by MMP cleavage during degradation or formation or an internal protein sequence. An overview of the assays used in this study and their technical specifications is given in Table 3. All samples were measured within the quantification range of each assay and any sample with values below the lower limit of detection (LLOD) was assigned the value of LLOD.

The above results demonstrate that ECM remodelling, assessed systemically by biomarkers of protein remodelling fragments, is accelerated during an exacerbation of COPD where disease activity is high.

Example 4: Pro-C6 in Diabetes Type II

Treatment of diabetic patients with full agonists of peroxisome proliferator-activated receptor gamma (PPARγ) improves insulin sensitivity, but is associated with weight gain, heart failure, peripheral oedema, and bone loss. Endotrophin, the C-terminal fragment of the α3 chain of procollagen type VI (also called Pro-C6), is involved in both adipose tissue matrix remodeling and metabolic control. We established a serum assay for endotrophin to assess if this novel adipokine could identify type 2 diabetes (DM2) patients who respond optimally to PPARγ agonists, improving the risk to benefit ratio.

Study Design

The BALLETS (Birmingham and Lambeth Liver Evaluation Testing Strategies) study was a phase III, randomized, double-blind, parallel-group, placebo and active comparator-controlled clinical study to determine the efficacy and safety of six months' treatment of balaglitazone or pioglitazone in subjects with type 2 diabetes on stable insulin therapy. The baseline demographics, CONSORT diagram as well as efficacy and safety data have previously been published (Henriksen, 2011). In the current study we used the per protocol population of the BALLETS study, which consisted of 299 subjects spread evenly over four groups (placebo, two doses of balaglitazone, and one dose of piogliatazone) as previously described (Henriksen, 2011), all with baseline and up to six follow-up parameters related to blood sugar control and Pro-C6 determinations under therapy.

Statistical Analysis

The analysis included subjects from the per protocol population having a baseline measurement of serum Pro-C6. Subjects were grouped into one of three tertiles based on their baseline Pro-C6 value. Tertile 1 included subjects with baseline serum Pro-C6 of 6.2 ng/mL or below; tertile 2 had baseline serum Pro-C6 of 6.3 ng/mL to 7.7 ng/mL, and tertile 3 had baseline serum Pro-C6 of 7.8 ng/mL or above. Baseline characteristics between the three subgroups were compared by analysis of variance (ANOVA), and comparison of the proportion of genders in each tertile was compared by Fisher's exact test.

Spearman's ranked correlation was conducted on baseline levels of serum Pro-C6, fasting serum glucose (FSG), blood HbA1c, body mass index (BMI), and the derived parameters of insulin resistance (HOMA-IR) and fatty liver index (FLI).

The HOMA-IR was calculated according to the homeostatis model assessment including serum glucose and insulin (Feigh, 2011) and FLI was calculated (as described by Bedogni et al, 2006) using the equation:

$$FLI = \frac{(e^{0.953*log_e(triglycerides)+0.139*BMI+0.718*log_e(ggt)+0.053*waist\ circumference-15.745})}{(1 + e^{0.953*log_e(triglycerides)+0.139*BMI+0.718*log_e(ggt)+0.053*waist\ circumference-15.745})} * 100$$

Changes from baseline in FSG, blood HbA1c, and serum Pro-C6 were studied as a function of time and treatment in each of the three tertiles. The least squares means (LS Means) and standard error were estimated from a mixed-effect repeated measure model with the change from baseline as the dependent variable; baseline level, visit (after 12 weeks on treatment) and end of treatment (after 26 weeks), and the baseline level vs visit and end of treatment vs visit interaction as fixed effects, and an unstructured covariance structure for subject.

For each subject the mean change from baseline was calculated as area under the curve by the trapezoidal method, and the LS means and standard error were estimated from an analysis of covariance model (ANCOVA) with the mean change as the dependent variable, the baseline level as the covariate, and treatments as fixed effects. Each tertile within each of the active treatment groups was compared with the placebo group with the level of significance adjusted for multiple comparisons by the Dunnett method. Assessment of whether mean change from baseline was different from 0 was based on the standard error of the LS means.

All statistical calculations were performed using the SAS software package. This study is registered with ClinicalTrials.gov identifier NCT00515632.

Results

Serum Endotrophin is Correlated to Metabolic Parameters.

Efficacy of treatment as assessed by metabolic parameters and safety data in the BALLET trial have been published previously (Henriksen, 2011). The baseline correlations of endotrophin to parameters associated with the metabolic syndrome are presented in Table 7.

TABLE 7

Demographics and baseline characteristics in subgroups of baseline PRO-C6

|  | Endotrophin (2.4-6.2 ng/mL) n = 96 | Endotrophin (6.3-7.7 ng/mL) n = 101 | Endotrophin (7.8-16 ng/mL) n = 100 | p-value |
|---|---|---|---|---|
| Treatment | Bala 10 mg: n = 27<br>Bala 20 mg: n = 22<br>Pio 45 mg: n = 24<br>Placebo n = 23 | Bala 10 mg: n = 21<br>Bala 20 mg: n = 21<br>Pio 45 mg: n = 29<br>Placebo n = 30 | Bala 10 mg: n = 25<br>Bala 20 mg: n = 25<br>Pio 45 mg: n = 31<br>Placebo n = 19 | — |
| Age (yrs) | 57.6 (8.1) | 60.6 (8.3) | 63.4 (80) | <0.0001 |
| Gender | Female: 21 (22%)<br>Male: 75 (78%) | Female: 32 (32%)<br>Male: 69 (68%) | Female: 43 (43%)<br>Male: 57 (57%) | p = 0.007 |
| BMI (kg/m$^2$) | 32.0 (3.9) | 33.6 (4.7) | 34.9 (6.3) | 0.0005 |
| Waist circumference (cm) | 110 (10) | 114 (12) | 117 (14) | 0.001 |
| Hip circumference (cm) | 109 (8) | 111 (10) | 115 (12) | 0.0002 |
| DXA total body fat mass (kg) | 30.8 (8.4) | 33.86 (8.9) | 36.1 (9.8) | 0.0006 |
| DXA trunk fat mass (kg) | 18.3 (5.2) | 20.0 (5.0) | 21.7 (5.6) | 0.0001 |
| Blood HbA1C (%) | 8.7 (1.4) | 8.4 (1.3) | 8.8 (1.5) | ns |
| Serum Glucose (mmol/L) | 9.4 (3.3) | 9.2 (3.2) | 9.8 (3.4) | Ns |
| Serum AST (U/L) | 28 (12) | 32 (13) | 32 (12) | Ns |
| Serum ALT (U/L) | 31 (15) | 34 (19) | 33 (17) | Ns |
| Serum GGT (U/L) | 45 (38) | 55 (56) | 54 (47) | Ns |
| Serum ALP (U/L) | 163 (49) | 172 (46) | 187 (56) | 0.004 |
| Serum Bilirubin (μmol/L) | 9 (3.3) | 9 (5.1) | 9 (3.7) | Ns |
| Serum Triglycerides (mmol/L) | 1.52 (0.94) | 1.85 (1.16) | 2 05 (1.07) | 0.002 |
| Serum Cholesterol (mmol/L)) | 4.34 (0.96) | 4.28 (0.85) | 4.45 (1.04) | Ns |
| Serum HDL Chol (mmol/L) | 1.31 (0.35) | 1.23 (0.29) | 1.25 (0.27) | Ns |
| Serum LDL Chol (mmol/L) | 2.61 (0.90) | 2.54 (0.76) | 2.61 (0.97) | Ns |

Endotrophin levels were significantly correlated to HOMA-IR, FLI, triglycerides, and BMI, but not to FSG and HbA1c, supporting that endotrophin is indeed an adipokine, related to adipocyte function, fat mass, and some aspects of insulin sensitivity. Endotrophin levels were not correlated to cholesterol levels or liver enzymes.

At the end of the six month treatment period, in the placebo group, the correlations between endotrophin and these metabolic parameters were maintained (Table 8, 9A). However, in those treated with either PPARγ agonist, the correlation between HOMA-IR and endotrophin was eliminated, while the correlation between endotrophin and BMI or FLI persisted and even showed a trend towards becoming stronger (Table 9B-9C).

TABLE 8

Spearman correlation coefficient (Rho) at baseline

| | Endo-trophin | Serum-glucose | Baseline-HbA1c | HOMA-IR | FLI | BMI |
|---|---|---|---|---|---|---|
| PRO-C6 | 1 | 0.07 | 0.06 | 0.16** | 0.32*** | 0.24*** |
| Serum-glucose | — | 1 | 0.47*** | 0.27*** | 0.20*** | 0.17** |
| Baseline-HbA1c | — | — | 1 | 0.15** | 0.17** | 0.10 |
| HOMA-IR | — | — | — | 1 | 0.42*** | 0.33*** |
| FLI | — | — | — | — | 1 | 0.86*** |
| BMI | — | — | — | — | — | 1 |

TABLE 9A

Spearman correlation coefficient at week 26 - Placebo group

| | Endo-trophin | Serum-Glucose | HbA1c | HOMA-IR | FLI | BMI |
|---|---|---|---|---|---|---|
| PRO-C6 | 1 | 0.05 | −0.07 | 0.28* | 0.34** | 0.26* |
| Serum-Glucose | — | 1 | 0.24* | 0.23* | 0.18 | 0.26* |
| HbA1c | — | — | 1 | 0.12 | 0.16 | 0.11 |
| HOMA-IR | — | — | — | 1 | 0.35** | 0.23 |
| FLI | — | — | — | — | 1 | 0.87*** |
| BMI | — | — | — | — | — | 1 |

TABLE 9B

Spearman correlation coefficient at week 26 - Pioglitazone 45 mg

| | Endo-trophin | Serum-Glucose | HbA1c | HOMA-IR | FLI | BMI |
|---|---|---|---|---|---|---|
| PRO-C6 | 1 | −0.21 | −0.31** | 0.02 | 0.39*** | 0.31** |
| Serum-Glucose | — | 1 | 0.48*** | 0.02 | −0.11 | −0.14 |
| HbA1c | — | — | 1 | −0.06 | −0.13 | −0.12 |
| HOMA-IR | — | — | — | 1 | 0.30** | 0.25* |
| FLI | — | — | — | — | 1 | 0.84*** |
| BMI | — | — | — | — | — | 1 |

Endotrophin Identifies Responders to Glitazone Therapy

Body weight and BMI were higher in the upper tertiles in all four treatment groups than in the lower tertile (Table 1). No differences were seen in glucose homeostasis between treatment groups.

Figure 7A:
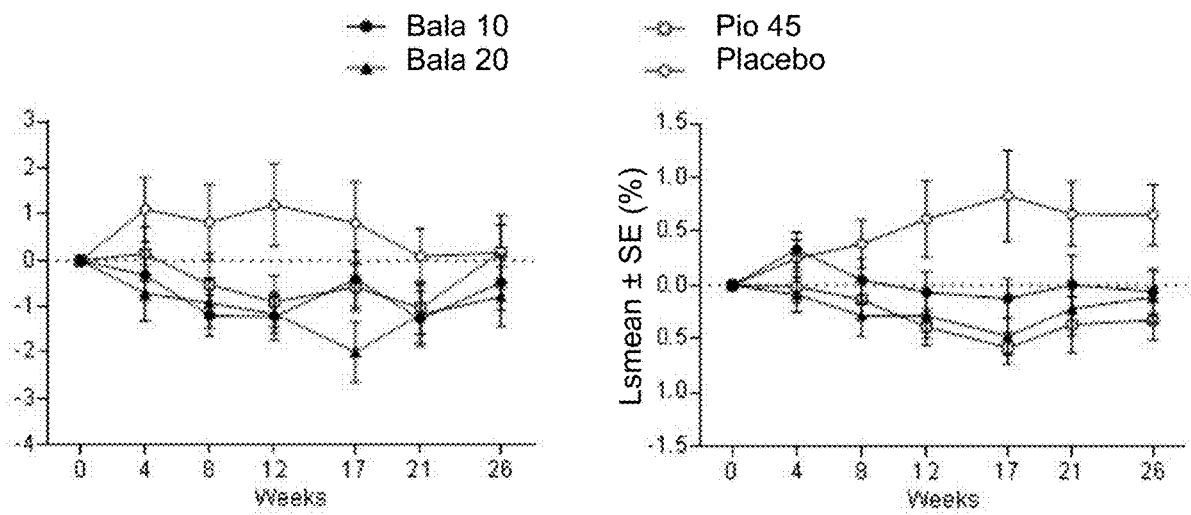
FIGS. 7A-7C show the effect on fasting serum glucose and blood HbA1c. Absolute change over time from baseline to end of treatment (week 26) in fasting serum glucose (left) and blood HbA1c (right) in subgroups (tertiles) baseline endotrophin <6.3 ng/mL (FIG. 7A), 6.3 to 7.7 ng/mL FIG. 7B) and >7.7 ng/mL (FIG. 7C) according to baseline serum Pro-C6.
Figure 7B:
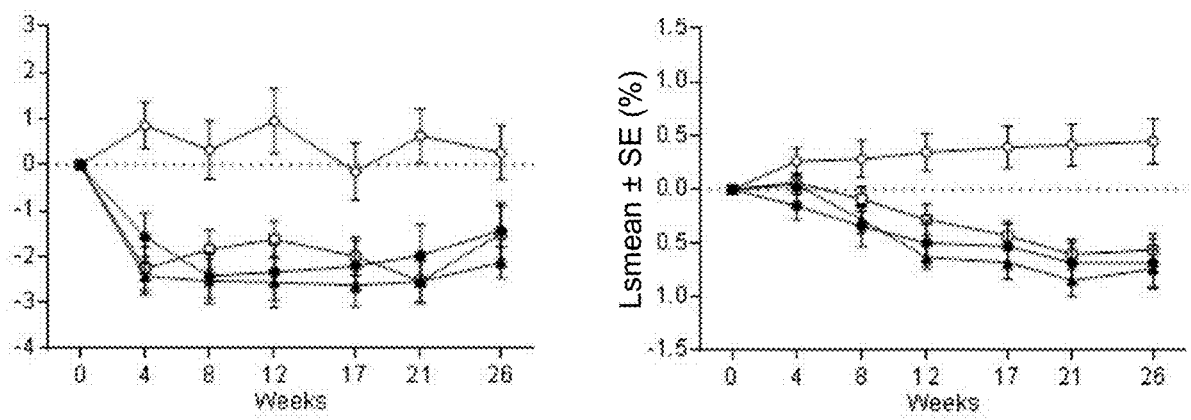
Figure 7C:
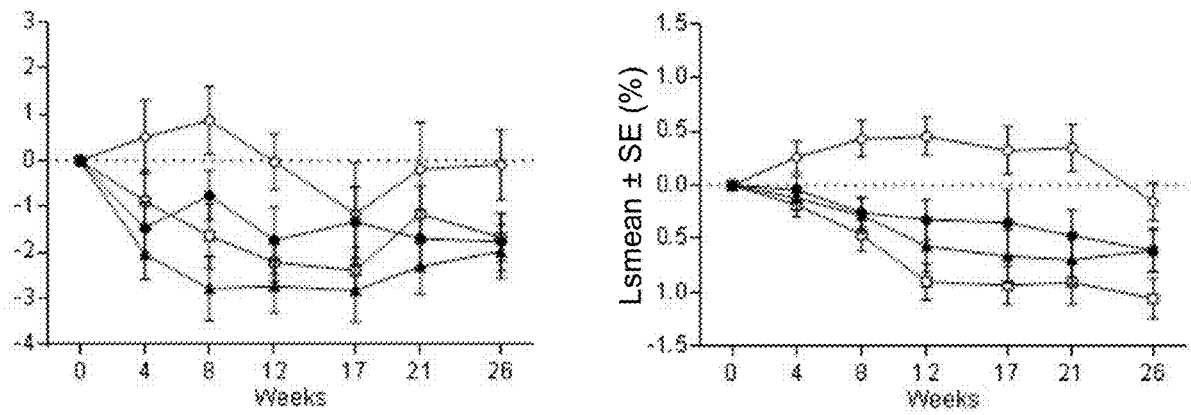

Absolute levels of FSG and HbA1c decreased in all three treatment arms as compared to placebo, but only in the two upper tertiles of endotrophin as compared to the baseline set as zero during the study (FIGS. 7A-7C).

When assessing the mean absolute change over time from baseline to end of treatment (week 26) in FSG (FIGS. 8A-8C, left), the reduction of FSG was larger (~2.5 mM) and statistically significant in the two upper tertiles when compared to the lower tertile, where the reduction compared to baseline was non-significant across all treatment groups. Similarly for HbA1c (FIGS. 8A-8C, right) the mean absolute change in endotrophin levels during the 26-week treatment period was significant only in the two upper tertiles and not in the lower tertile, both when comparing to placebo and to baseline levels. When response to therapy was investigated, patients in the upper two tertiles of baseline serum endotrophin were significantly more likely to show a clinically significant response to glitazone therapy. In these patients the odds ratios for a more than 1% and 0.5% decrease of HbA1c were 4.1 (p<0.001) and 4.3 (p<0.001), respectively (FIG. 9). When assessing the change in insulin sensitivity (by HOMA-IR) under therapy, again the subjects in the upper tertiles of endotrophin showed the best improvement (FIG. 10A-10C), with the highest tertile marginally missing statistical significance. Interestingly, despite variant efficacy of the therapy there were no marked differences in weight gain between the tertiles of endotrophin levels (data not shown).

The effect on serum endotrophin as a function of treatment and time (to study midpoint and end of treatment), expressed as percent change relative to baseline, is shown in FIGS. 11A-11F. Levels of endotrophin increased in both the placebo and the treatment groups for the two lowest tertiles, but not in the highest tertile.

Adverse Events

Lower leg edema, when measured as volume increase due to water displacement, was correlated with baseline serum endotrophin tertiles. Glitazone therapy led to increased lower leg volume in the lower and middle tertile, while there were no differences between treatment and placebo groups in the upper tertile (FIG. 12A-12C). AEs and severe AEs (SAEs) in the different tertiles of serum endotrophin are presented in Table 10. There were no significant differences in the occurrence of AEs or SAEs in the three different treatment groups when stratified according to endotrophin levels. The difference between the SAEs in Table 10 and the lower leg oedema reported in FIGS. 12A-12C is a function of the lower leg volume being a quantitative measure and the reporting of oedemas being a patient reported output (FIGS. 10A-10C).

TABLE 10

Adverse event profile in subgroups of baseline endotrophin in each treatment group

N (%) E

| | Placebo | Balaglitazone 10 mg | Balaglitazone 20 mg | Pioglitazone 45 mg |
|---|---|---|---|---|
| Tertile 1: AEs | | | | |
| # Subjects | n = 23 | n = 27 | n = 22 | n = 24 |
| All AEs | 16 (70%) 30 | 20 (74%) 38 | 17 (77%) 33 | 19 (79%) 45 |
| Serious AEs | 0 (0%) 0 | 1 (4%) 1 | 1 (5%) 1 | 1 (4%) 1 |
| Tertile 2: AEs | | | | |
| # Subjects | n = 30 | n = 21 | n = 21 | n = 29 |
| All AEs | 23 (77%) 51 | 17 (81%) 35 | 15 (71%) 36 | 17 (59%) |
| Serious AEs | 3 (10%) 3 | 1 (5%) 1 | 0 (0%) 0 | 2 (6%) 3 |
| Tertile 3: AEs | | | | |
| # Subjects | n = 19 | n = 25 | n = 25 | n = 31 |
| All AEs | 14 (74%) 41 | 20 (60%) 55 | 20 (60%) 43 | 25 (81%) |
| Serious AEs | 0 (0%) 0 | 1 (4%) 1 | 6 (24%) 6 | 4 (13%) 6 |
| Tertile 1: Severe AEs | | | | |
| Heart failure | 0 (0%) 0 | 0 (0%) 0 | 0 (0%) 0 | 0 (0%) 0 |
| Cardiac ischaemia | 1 (4%) 1 | 0 (0%) 0 | 2 (9%) 2 | 0 (0%) 0 |
| Peripheral oedema | 0 (0%) 0 | 2 (7%) 2 | 2 (9%) 2 | 5 (21%) 5 |
| Total severe AEs | 1 (4%) 1 | 2 (7%) 2 | 4 (18%) 4 | 5 (21%) 5 |
| Tertile 2: Severe AEs | | | | |
| Heart failure | 0 (0%) 0 | 0 (0%) 0 | 0 (0%) 0 | 0 (0%) 0 |
| Cardiac ischaemia | 1 (3%) 1 | 1 (5%) 1 | 0 (0%) 0 | 1 (3%) 1 |
| Peripheral oedema | 1 (3%) 1 | 3 (14%) 3 | 2 (10%) 2 | 5 (17%) 5 |
| Total severe AEs | 2 (7%) 2 | 4 (19%) 4 | 2 (10%) 2 | 5 (17%) 6 |
| Tertile 3: Severe AEs | | | | |
| Heart failure | 0 (0%) 0 | 0 (0%) 0 | 0 (0%) 0 | 1 (3%) 1 |
| Cardiac ischaemia | 1 (5%) 1 | 0 (0%) 0 | 1 (4%) 1 | 3 (10%) 4 |
| Peripheral oedema | 1 (5%) 2 | 1 (8%) 1 | 1 (4%) 1 | 2 (6%) 2 |
| Total severe AEs | 2 (11%) 3 | 1 (8%) 1 | 2 (8%) 2 | 6 (19%) 7 |

Discussion

Serum endotrophin (Pro-C6) was predictive of a response to the insulin sensitizers, pioglitazone and balaglitazone, in patients with type 2 diabetes. Thus, patients with Pro-C6 serum levels in the two upper tertiles were 4 times more likely to have a treatment response when compared to patients in the lower tertile. As the glitazones are associated with safety concerns such as non-fatal heart failure and bone fractures, identifying the optimal responders who will gain the most treatment benefit with the fewest AEs is crucial for the continued use of these drugs, which still are considered highly effective insulin sensitizers. In direct agreement, patients in the upper tertiles of baseline Pro-C6 who responded with a decrease of FPG and HbA1c tertile developed no increase in lower leg oedema, one of the major AEs with glitazone treatment. These efficacy and safety data combined are highly relevant for an improved benefit to side effect prediction for patients treated with glitazones; this should also apply when their repurposing for other indications, especially the treatment of non-alcoholic steatohepatitis (NASH) is considered.

Endotrophin mediated metabolic dysfunction in obesity is likely induced via induction of a pro-inflammatory state and fibrosis in adipose tissue coupled with a reduction of energy expenditure. Accordingly, its suppression improved insulin sensitivity and attenuated adipose tissue inflammation (Sun, 2014), which correlates well with our findings that elevated serum endotrophin levels are indicative of a response to PPARγ agonists. Furthermore, mRNA levels of the endotrophin precursor, procollagen α3(VI), are upregulated in obese adipose tissue, again paralleling adipose tissue inflammation and fibrosis, supporting an important role of procollagen type VI as a modulator of adipocytes and adipose tissue in general (Dankel, 2014). The ECM and especially procollagen type VI and endotrophin may be of particular relevance in fatty liver disease and its severe expression, NASH, a metabolic-fibrotic disorder of the liver that shows at least a partial overlap with type 2 diabetes. Accordingly, we expect that this novel biomarker will also assist in the diagnosis and management of NASH patients, where insulin sensitizers may be beneficial for subpopulations, both for the treatment of insulin resistance and liver fibrosis. Here, the ECM, in particular collagens/collagen type VI, and their functional role in transition of fatty liver to overt fibrotic NASH needs to be further investigated. In agreement, in the current study, we observed a strong correlation to serum triglycerides and the FLI index that correlates with NASH inflammatory activity and predicts more severe liver fibrosis (Bedogni, 2006). In support of a role for type VI collagen in NASH-related fibrosis, prior studies demonstrated its prominent expression in areas of active scar formation (Burt, 1990; Griffiths, 1992) and elevated serum levels of the collagen VI core structure (which lacks the endotrophin domain) have been shown to be associated with advanced liver fibrosis in rodents (Veidal, 2011) and patients (Lebensztejn, 2006; Stickel, 2001), and with elevated portal pressure (Leeming, 2013). The expression of procollagen α3(VI) is regulated by PPARγ which is in direct alignment with our findings. In fact, procollagen α3(VI) mRNA is suppressed by PPARγ, as demonstrated by an increase in its mRNA in adipocyte cultures treated with a siRNA against PPARγ and by a decrease in its transcripts in subcutaneous adipose tissue of patients with type 2 diabetes treated with the PPARγ agonist pioglitazone, especially in patients with high baseline tissue levels of procollagen α3(VI) mRNA. These data may in part explain the change in correlations, from baseline to the end of treatment, between endotrophin/Pro-C6 serum levels and HbA1c or HOMA-IR, in particular the lack of a correlation between endotrophin and the metabolic parameters following glitazone treatment. Thus the expression of the endotrophin precursor (as measured by procollagen α3(VI) mRNA) in peripheral adipose tissue was not dependent on BMI or total fat mass in severely obese, insulin-resistant patients. In another clinical study tissue endotrophin levels in obese subjects correlated with chronic inflammation and systemic insulin resistance (Park, 2013). Further proof of the direct link between procollagen VI, adipose tissue fibrosis and impaired glucose sensitivity is provided by a study in ob/ob mice (that lack a functional leptin gene) in the absence of collagen VI in white adipose tissue. These mice had a significantly improved insulin sensitivity in the absence of adipose tissue fibrosis and inflammation (Khan, 2009). On a first view these data appear to contradict the strong correlation between serum endotrophin and BMI, FLI, and HOMA-IR, as found in our study. However, the presence of procollagen VI is only a necessary but not a sufficient precondition for the proteolytic generation of the adipokine endotrophin. Therefore, it will be of interest to identify the endotrophin generating protease and to characterize its upstream regulation. In addition, leptin induced the expression of type VI procollagen, which further supports a link between leptin resistance, metabolic dysfunction, and endotrophin.

As discussed before, the ECM has until now mostly been considered a passive scaffold. Type VI collagen has mostly been recognized through mutations in the genes COL6A1, COL6A2, and COL6A3 that encode its three constituent chains, which cause muscle disorders such as Bethlem myopathy, Ullrich congenital muscular dystrophy, limb-girdle muscular dystrophy, and autosomal recessive myosclerosis. (Lampe, 2005; Bonaldo, 1998; Bushby, 2014). This provides an interesting link to metabolic dysfunction since muscle represents an important regulator of insulin resistance. Therefore, all available evidence strongly suggests that collagen type VI is more than a passive ECM component, but an important mediator of adipose (and liver) metabolic dysfunction related to insulin resistance, type 2 diabetes, and NASH.

In conclusion, circulating endotrophin which prominently derives from adipocytes and adipose tissue is elevated in relation to insulin resistance and predictive of the response to insulin sensitizers. This permits identification and monitoring of patients who will respond optimally to an insulin sensitizer, which improves the benefit to risk ratio of PPARγ agonists in the treatment of type 2 diabetes and likely NASH.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCES

1. Agrawal R, Jain P, Dikshit S N. Balaglitazone: a second generation peroxisome proliferator-activated receptor (PPAR) gamma (gamma) agonist. Mini Rev Med Chem 2012 February; 12(2):87-97.
2. Aigner T, Hambach L, Soder S, Schlotzer-Schrehardt U, Poschl E. The C5 domain of Col6A3 is cleaved off from the Col6 fibrils immediately after secretion. Biochem Biophys Res Commun 2002; 290: 743-8.
3. Armbrecht G, Belavy D L, Gast U, et al. (2010) Resistive vibration exercise attenuates bone and muscle atrophy in 56 days of bed rest: biochemical markers of bone metabolism. Osteoporos Int 21:597-607. doi: 10.1007/s00198-009-0985-z
4. Atkinson J C, Ruhl M, Becker J, Ackermann R, Schuppan D. Collagen VI regulates normal and transformed mesenchymal cell proliferation in vitro. Exp Cell Res 1996 Nov. 1; 228: 283-291.
5. Barascuk N, Genovese F, Larsen L, Byrjalsen I, Zheng Q, Sun S, Hosbond S, Poulsen T S, Diederichsen A, Jensen J M, Mickley H, Register T C, Rasmussen L M, Leeming D J, Christiansen C, Karsdal M A. A MMP derived versican neo-epitope is elevated in plasma from patients with atherosclerotic heart disease. Int J Clin Exp Med 2013; 6: 174-184.
6. Barascuk N, Veidal S S, Larsen L, et al. A novel assay for extracellular matrix remodeling associated with liver fibrosis: An enzyme-linked immunosorbent assay (ELISA) for a MMP-9 proteolytically revealed neo-epitope of type III collagen. Clin Biochem 2010; 43: 899-904.
7. Bedogni G, Bellentani S, Miglioli L, Masutti F, Passalacqua M, Castiglione A et al. The Fatty Liver Index: a simple and accurate predictor of hepatic steatosis in the general population. BMC Gastroenterol 2006; 6:33.
8. Belavy D L, Miokovic T, Armbrecht G, et al. (2009) Resistive vibration exercise reduces lower limb muscle atrophy during 56-day bed-rest. Journal of musculoskeletal & neuronal interactions 9:225-235.
9. Berger J P, Akiyama T E, Meinke P T. PPARs: therapeutic targets for metabolic disease. Trends Pharmacol Sci 2005 May; 26(5):244-51.
10. Bhasin S, He E J, Kawakubo M, et al. (2009) N-terminal propeptide of type III procollagen as a biomarker of anabolic response to recombinant human GH and testosterone. J Clin Endocrinol Metab 94:4224-4233. doi: 10.1210/jc.2009-1434
11. Bidanset D J, Guidry C, Rosenberg L C, et al. Binding of the proteoglycan decorin to collagen type VI. J Biol Chem 1992; 267: 5250-6.
12. Bonaldo P, Russo V, Bucciotti F, Doliana R, Colombatti A. Structural and functional features of the alpha 3 chain indicate a bridging role for chicken collagen VI in connective tissues. Biochemistry 1990; 29: 1245-54.
13. Bonaldo P, Sandri M (2012) Cellular and molecular mechanisms of muscle atrophy. Dis Model Mech 6:25-39. doi: 10.1242/dmm.010389

14. Burt A D, Griffiths M R, Schuppan D, Voss B, MacSween R N. Ultrastructural localization of extracellular matrix proteins in liver biopsies using ultracryomicrotomy and immuno-gold labelling. Histopathology 1990 January; 16(1):53-8.
15. Bushby K M, Collins J, Hicks D. Collagen type VI myopathies. Adv Exp Med Biol 2014; 802:185-99
16. Carter R I, Ungurs M J, Mumford R A, Stockley R A. Aalpha-Val360: a marker of neutrophil elastase and COPD disease activity. Eur Respir J 2013 January; 41: 31-38.
17. Charbonnel B, DeFronzo R, Davidson J, Schmitz O, Birkeland K, Pirags V et al. Pioglitazone use in combination with insulin in the prospective pioglitazone clinical trial in macrovascular events study (PROactive19). J Clin Endocrinol Metab 2010 May; 95(5):2163-71.
18. Chen F, Lam R, Shaywitz D, et al. Evaluation of early biomarkers of muscle anabolic response to testosterone. J Cachexia Sarcopenia Muscle 2011; 2: 45-56.
19. Cho N, Momose Y. Peroxisome proliferator-activated receptor gamma agonists as insulin sensitizers: from the discovery to recent progress. Curr Top Med Chem 2008; 8(17):1483-507.
20. Corhay J L, Moermans C, Henket M, Nguyen D D, Duysinx B, Louis R. Increased of exhaled breath condensate neutrophil chemotaxis in acute exacerbation of COPD. Respir Res 2014; 15: 115.
21. Cox T R, Erler J T. Remodeling and homeostasis of the extracellular matrix: implications for fibrotic diseases and cancer. Dis Model Mech 2011 March; 4: 165-178.
22. Cruz-Jentoft A J, Baeyens J P, Bauer J M, et al. Sarcopenia: European consensus on definition and diagnosis: Report of the European Working Group on Sarcopenia in Older People. Age Ageing 2010; 39: 412-23.
23. Dankel S N, Svard J, Mattha S, Claussnitzer M, Kloting N, Glunk V et al. COL6A3 expression in adipocytes associates with insulin resistance and depends on PPARgamma and adipocyte size. Obesity (Silver Spring) 2014 August; 22(8):1807-13.
24. Donaldson G C, Seemungal T A, Bhowmik A, Wedzicha J A. Relationship between exacerbation frequency and lung function decline in chronic obstructive pulmonary disease. Thorax 2002 October; 57: 847-852.
25. Donaldson G C, Wedzicha J A. COPD exacerbations 0.1: Epidemiology. Thorax 2006 February; 61: 164-168.
26. Engvall E, Hessle H, Klier G. Molecular assembly, secretion, and matrix deposition of type VI collagen. J Cell Biol 1986 March; 102: 703-710.
27. Feigh M, Henriksen K, Andreassen K V, Hansen C, Henriksen J E, Beck-Nielsen H et al. A novel oral form of salmon calcitonin improves glucose homeostasis and reduces body weight in diet-induced obese rats. Diabetes Obes Metab 2011 October; 13(10):911-20.
28. Gefter M L, Margulies D H, Scharff M D. A simple method for polyethylene glycol-promoted hybridization of mouse myeloma cells. Somatic Cell Genet 1977; 3: 231-6.
29. Gelse K, Poschl E, Aigner T. Collagens—structure, function, and biosynthesis. Adv Drug Deliv Rev 2003; 55: 1531-46.
30. Giannelli G, De M A, Marinosci F, Antonaci S. Matrix metalloproteinase imbalance in muscle disuse atrophy. Histol Histopathol 2005; 20: 99-106.
31. Global Initiative for Chronic Obstructive Lung Disease (GOLD). Global Strategy for the Diagnosis, Management and Prevention of COPD. www.goldcopd.org. Date last updated: January 2014. Date last accessed: Oct. 22 2014.
32. Granzier H L, Irving T C. Passive tension in cardiac muscle: contribution of collagen, titin, microtubules, and intermediate filaments. Biophys J 1995; 68: 1027-44.
33. Griffiths M R, Shepherd M, Ferrier R, Schuppan D, James O F, Burt A D. Light microscopic and ultrastructural distribution of type VI collagen in human liver: alterations in chronic biliary disease. Histopathology 1992 October; 21(4):335-44.
34. Hallgren O, Nihlberg K, Dahlback M, Bjermer L, Eriksson L T, Erjefalt J S, Lofdahl C G, Westergren-Thorsson G. Altered fibroblast proteoglycan production in COPD. Respir Res 2010; 11:55.
35. Heinemeier K M, Olesen J L, Haddad F, et al. (2009) Effect of unloading followed by reloading on expression of collagen and related growth factors in rat tendon and muscle. J Appl Physiol 106:178-186. doi: 10.1152/japplphysiol.91092.2008
36. Henriksen K, Byrjalsen I, Qvist P, Beck-Nielsen H, Hansen G, Riis B J et al. Efficacy and safety of the PPARgamma partial agonist balaglitazone compared with pioglitazone and placebo: a phase III, randomized, parallel-group study in patients with type 2 diabetes on stable insulin therapy. Diabetes Metab Res Rev 2011 May; 27(4):392-401.
37. Home P D, Pocock S J, Beck-Nielsen H, Curtis P S, Gomis R, Hanefeld M et al. Rosiglitazone evaluated for cardiovascular outcomes in oral agent combination therapy for type 2 diabetes (RECORD): a multicentre, randomised, open-label trial. Lancet 2009 Jun. 20; 373 (9681):2125-35.
38. Hortobagyi T, Dempsey L, Fraser D, et al. (2000) Changes in muscle strength, muscle fibre size and myofibrillar gene expression after immobilization and retraining in humans. J Physiol 524 Pt 1:293-304.
39. Huang R, Merrilees M J, Braun K, Beaumont B, Lemire J, Clowes A W, Hinek A, Wight T N. Inhibition of versican synthesis by antisense alters smooth muscle cell phenotype and induces elastic fiber formation in vitro and in neointima after vessel injury. Circ Res 2006 Feb. 17; 98: 370-377.
40. Hughes V A, Frontera W R, Roubenoff R, Evans W J, Singh M A. Longitudinal changes in body composition in older men and women: role of body weight change and physical activity. Am J Clin Nutr 2002; 76: 473-81.
41. Hurst J R, Vestbo J, Anzueto A, Locantore N, Mullerova H, Tal-Singer R, Miller B, Lomas D A, Agusti A, Macnee W, Calverley P, Rennard S, Wouters E F, Wedzicha J A. Susceptibility to exacerbation in chronic obstructive pulmonary disease. N Engl J Med 2010 Sep. 16; 363: 1128-1138.
42. Karalliedde J, Buckingham R E. Thiazolidinediones and their fluid-related adverse effects: facts, fiction and putative management strategies. Drug Saf 2007; 30(9):741-53.
43. Karsdal M A, Delvin E, Christiansen C. Protein fingerprints—relying on and understanding the information of serological protein measurements. Clin Biochem 2011 November; 44: 1278-1279.
44. Karsdal M A, Manon-Jensen T, Genovese F, Kristensen J H, Nielsen M J, Sand J M et al. Novel insights into the function and dynamics of extracellular matrix in liver fibrosis. Am J Physiol Gastrointest Liver Physiol 2015 May 15; 308(10):G807-G830.
45. Karsdal M A, Nielsen M J, Sand J M, Henriksen K, Genovese F, Bay-Jensen A C, Smith V, Adamkewicz J I, Christiansen C, Leeming D J. Extracellular matrix remodeling: the common denominator in connective tissue 46. Keene D R, Engvall E, Glanville R W. Ultrastructure of type VI collagen in human skin and cartilage suggests an anchoring function for this filamentous network. J Cell Biol 1988; 107: 1995-2006.
47. Kenagy R D, Plaas A H, Wight T N. Versican degradation and vascular disease. Trends Cardiovasc Med 2006 August; 16: 209-215.
48. Khan T, Muise E S, Iyengar P, Wang Z V, Chandalia M, Abate N et al. Metabolic dysregulation and adipose tissue fibrosis: role of collagen VI. Mol Cell Biol 2009 March; 29(6):1575-91.
49. Kuo H J, Maslen C L, Keene D R, Glanville R W. Type VI collagen anchors endothelial basement membranes by interacting with type IV collagen. J Biol Chem 1997; 272: 26522-9.
50. Lamande S R, Morgelin M, Adams N E, Selan C, Allen J M. The C5 domain of the collagen VI alpha3(VI) chain is critical for extracellular microfibril formation and is present in the extracellular matrix of cultured cells. J Biol Chem 2006; 281: 16607-14.
51. Lampe A K, Bushby K M D (2005) Collagen VI related muscle disorders. J Med Genet 42:673-685. doi: 10.1136/jmg.2002.002311
52. Larsen P J, Lykkegaard K, Larsen L K, Fleckner J, Sauerberg P, Wassermann K et al. Dissociation of anti-hyperglycaemic and adverse effects of partial perioxisome proliferator-activated receptor (PPAR-gamma) agonist balaglitazone. Eur J Pharmacol 2008 Oct. 31; 596(1-3): 173-9.
53. Lebensztejn D M, Sobaniec-Lotowska M E, Kaczmarski M, Voelker M, Schuppan D. Matrix-derived serum markers in monitoring liver fibrosis in children with chronic hepatitis B treated with interferon alpha. World J Gastroenterol 2006 Jun. 7; 12(21):3338-43.
54. Leeming D J, Nielsen M J, Dai Y, Veidal S S, Vassiliadis E, Zhang C, He Y, Vainer B, Zheng Q, Karsdal M A. Enzyme-linked immunosorbent serum assay specific for the 7S domain of Collagen Type IV (P4NP 7S): A marker related to the extracellular matrix remodeling during liver fibrogenesis. Hepatol Res 2012 May; 42: 482-493.
55. Leeming D J, Sand J M, Nielsen M J, Genovese F, Martinez F J, Hogaboam C M, Han M K, Klickstein L B, Karsdal M A. Serological investigation of the collagen degradation profile of patients with chronic obstructive pulmonary disease or idiopathic pulmonary fibrosis. Biomark Insights 2012; 7: 119-126.
56. Leeming D J, Karsdal M A, Byrjalsen I, Bendtsen F, Trebicka J, Nielsen M J et al. Novel serological neo-epitope markers of extracellular matrix proteins for the detection of portal hypertension. Aliment Pharmacol Ther 2013 November; 38(9):1086-96.
57. Mak K M, Sehgal P, Harris C K. Type VI Collagen: Its Biology and Value as a Biomarker of Hepatic Fibrosis. Austin Biomark Diagn. 1[2], 9.2014.
58. Mercer P F, Shute J K, Bhowmik A, Donaldson G C, Wedzicha J A, Warner J A. MMP-9, TIMP-1 and inflammatory cells in sputum from COPD patients during exacerbation. Respir Res 2005; 6: 151.
59. Merrilees M J, Ching P S, Beaumont B, Hinek A, Wight T N, Black P N. Changes in elastin, elastin binding protein and versican in alveoli in chronic obstructive pulmonary disease. Respir Res 2008; 9: 41.
60. Miller B F, Olesen J L, Hansen M, et al. (2005) Coordinated collagen and muscle protein synthesis in human patella tendon and quadriceps muscle after exercise. J Physiol (Lond) 567:1021-1033. doi: 10.1113/jphysiol.2005.093690
61. Miller T A, Lesniewski L A, Muller-Delp J M, et al. (2001) Hindlimb unloading induces a collagen isoform shift in the soleus muscle of the rat. AJP: Regulatory, Integrative and Comparative Physiology 281:R1710-R1717.
62. Nedergaard A, Karsdal M A, Sun S, Henriksen K. Serological muscle loss biomarkers: an overview of current concepts and future possibilities. J Cachexia Sarcopenia Muscle 2013; 4: 1-17.
63. Nedergaard A, Sun S, Karsdal M A, et al. (2013) Type VI collagen turnover-related peptides-novel serological biomarkers of muscle mass and anabolic response to loading in young men. J Cachexia Sarcopenia Muscle 4:267-275. doi: 10.1007/s13539-013-0114-x
64. Nielsen M J, Nedergaard A F, Sun S, et al. (2013) The neo-epitope specific PRO-C3 ELISA measures true formation of type III collagen associated with liver and muscle parameters. Am J Transl Res 5:303-315.
65. Niemela O, Risteli L, Parkkinen J, Risteli J. Purification and characterization of the N-terminal propeptide of human type III procollagen. Biochem J 1985; 232: 145-50.
66. O'Reilly P J, Jackson P L, Wells J M, Dransfield M T, Scanlon P D, Blalock J E. Sputum PGP is reduced by azithromycin treatment in patients with COPD and correlates with exacerbations. BMJ Open 2013; 3: e004140.
67. Orkin R W, Gehron P, McGoodwin E B, Martin G R, Valentine T, Swarm R. A murine tumor producing a matrix of basement membrane. J Exp Med 1977 Jan. 1; 145: 204-220.
68. Pasarica M, Gowronska-Kozak B, Burk D, Remedios I, Hymel D, Gimble J et al. Adipose tissue collagen VI in obesity. J Clin Endocrinol Metab 2009 December; 94(12): 5155-62.
69. Park J, Scherer P E. Adipocyte-derived endotrophin promotes malignant tumor progression. J Clin Invest 2012 November; 122(11):4243-56.
70. Park J, Scherer P E. Endotrophin in the tumor stroma: a new therapeutic target for breast cancer? Expert Rev Anticancer Ther 2013 February; 13(2):111-3.
71. Pfister R R, Haddox J L, Sommers C I, Lam K W. Identification and synthesis of chemotactic tripeptides from alkali-degraded whole cornea. A study of N-acetyl-proline-glycine-proline and N-methyl-proline-glycine-proline. Invest Ophthalmol Vis Sci 1995 June; 36: 1306-1316.
72. Rennie M J, Selby A, Atherton P, et al. Facts, noise and wishful thinking: muscle protein turnover in aging and human disuse atrophy. Scand J Med Sci Sports 2010; 20: 5-9.
73. Reznick A Z, Menashe O, Bar-Shai M, Coleman R, Carmeli E. Expression of matrix metalloproteinases, inhibitor, and acid phosphatase in muscles of immobilized hindlimbs of rats. Muscle Nerve 2003; 27: 51-9.
74. Rittweger J, Belavy D, Hunek P, et al. Highly demanding resistive vibration exercise program is tolerated during 56 days of strict bed-rest. Int J Sports Med 2006; 27: 553-9.
75. Ruhl M, Johannsen M, Atkinson J, Manski D, Sahin E, Somasundaram R, Riecken E O, Schuppan D. Soluble collagen VI induces tyrosine phosphorylation of paxillin 76. Ruhl M, Sahin E, Johannsen M, Somasundaram R, Manski D, Riecken E O, Schuppan D. Soluble collagen VI drives serum-starved fibroblasts through S phase and prevents apoptosis via down-regulation of Bax. J Biol Chem 1999 Nov. 26; 274: 34361-34368.
77. Sand J M, Larsen L, Hogaboam C, Martinez F, Han M, Rossel L M, Nawrocki A, Zheng Q, Karsdal M A, Leeming D J. MMP mediated degradation of type IV collagen alpha 1 and alpha 3 chains reflects basement membrane remodeling in experimental and clinical fibrosis—validation of two novel biomarker assays. PLoS One 2013; 8: e84934.
78. Savolainen J, Vaananen K, Vihko V, et al. (1987) Effect of immobilization on collagen synthesis in rat skeletal muscles. American Journal of Physiology—Regulatory, Integrative and Comparative Physiology 252:R883-R888.
79. Scharf G, Heineke J. Finding good biomarkers for sarcopenia. J Cachexia Sarcopenia Muscle 2012; 3: 145-8.
80. Seemungal T A, Donaldson G C, Paul E A, Bastall J C, Jeffries D J, Wedzicha J A. Effect of exacerbation on quality of life in patients with chronic obstructive pulmonary disease. Am J Respir Crit Care Med 1998 May; 157: 1418-1422.
81. Soler-Cataluna J J, Martinez-Garcia M A, Roman S P, Salcedo E, Navarro M, Ochando R. Severe acute exacerbations and mortality in patients with chronic obstructive pulmonary disease. Thorax 2005 November; 60: 925-931.
82. Soroceanu M A, Miao D, Bai X Y, Su H, Goltzman D, Karaplis A C. Rosiglitazone impacts negatively on bone by promoting osteoblast/osteocyte apoptosis. J Endocrinol 2004 October; 183(1):203-16.
83. Stallcup W B, Dahlin K, Healy P. Interaction of the NG2 chondroitin sulfate proteoglycan with type VI collagen. J Cell Biol 1990; 111: 3177-88.
84. Stickel F, Urbaschek R, Schuppan D, Poeschl G, Oesterling C, Conradt C et al. Serum collagen type VI and XIV and hyaluronic acid as early indicators for altered connective tissue turnover in alcoholic liver disease. Dig Dis Sci 2001 September; 46(9):2025-32.
85. Sun K, Park J, Gupta O T, Holland W L, Auerbach P, Zhang N et al. Endotrophin triggers adipose tissue fibrosis and metabolic dysfunction. Nat Commun 2014; 5:3485.
86. Takada I, Suzawa M, Matsumoto K, Kato S. Suppression of PPAR transactivation switches cell fate of bone marrow stem cells from adipocytes into osteoblasts. Ann N Y Acad Sci 2007 November; 1116:182-95.
87. Takamatsu S, Nakabayashi H, Okamoto Y, Nakano H. Noninvasive determination of liver collagen content in chronic hepatitis. Multivariate regression modeling with blood chemical parameters as variables. J Gastroenterol 1997 June; 32: 355-360.
88. Tapanainen P, Knip M, Risteli L, et al. (1997) Collagen metabolites in the prediction of response to G H therapy in short children. Eur J Endocrinol 137:621-625.
89. Tetley T D. Inflammatory cells and chronic obstructive pulmonary disease. Curr Drug Targets Inflamm Allergy 2005 December; 4: 607-618.
90. Urciuolo A, Quarta M, Morbidoni V, et al. (2013) Collagen VI regulates satellite cell self-renewal and muscle regeneration. Nat Commun 4:1964. doi: 10.1038/ncomms2964
91. Veidal S S, Karsdal M A, Vassiliadis E, et al. MMP mediated degradation of type VI collagen is highly associated with liver fibrosis—identification and validation of a novel biochemical marker assay. PLoS One 2011; 6: e24753.
92. Vestbo J, Rennard S. Chronic obstructive pulmonary disease biomarker(s) for disease activity needed—urgently. Am J Respir Crit Care Med 2010 Oct. 1; 182: 863-864.
93. Welle S. Cellular and molecular basis of age-related sarcopenia. Can J Appl Physiol 2002; 27: 19-41.
94. Williams P, Goldspink G (1981) Connective tissue changes in surgically overloaded muscle. Cell Tissue Res 221:465-470. doi: 10.1007/BF00216749

The invention claimed is:

1. An isolated monoclonal antibody that specifically binds a C-terminal epitope of the C5 domain of the a3 chain of collagen Type 6, wherein the antibody comprises
   (a) a variable heavy chain region comprising CDRH1 comprising the amino acid sequence of SEQ ID NO.: 6, CDRH2 comprising the amino acid sequence of SEQ ID NO.: 7, and CDRH3 comprising the amino acid sequence of SEQ ID NO.: 8; and
   (b) a variable light chain region comprising CDRL1 comprising the amino acid sequence of SEQ ID NO.: 10, CDRL2 comprising the amino acid sequence of SEQ ID NO.: 11, and CDRL3 comprising the amino acid sequence of SEQ ID NO.: 12,
   wherein the antibody specifically binds the amino acid sequence consisting of SEQ ID NO:1.

2. The monoclonal antibody of claim 1, wherein said antibody does not specifically bind an elongated version of said C-terminal amino acid sequence consisting of SEQ ID. NO:2.

3. The monoclonal antibody of claim 1, wherein the ratio of the affinity of the antibody for amino acid sequence of SEQ ID. NO:1 to the affinity of said antibody for elongated amino acid sequence of SEQ ID. NO:2 is greater than 10 to 1.

4. The monoclonal antibody of claim 1, wherein said antibody does not specifically bind a truncated version of said C-terminal amino acid sequence consisting of SEQ ID. NO:3.

5. The monoclonal antibody of claim 1, wherein the ratio of the affinity of the antibody for amino acid sequence of SEQ ID. NO:1 to the affinity of said antibody for truncated amino acid sequence of SEQ ID. NO:3 is greater than 10 to 1.

6. An immunoassay method for detecting in a sample a C-terminal epitope of the C5 domain of the a3 chain of collagen type VI, wherein said method comprises performing an immunoassay comprising: contacting a sample comprising said C-terminal epitope of the a3 chain of collagen type VI with the isolated monoclonal antibody as claimed in claim 1; and
   determining binding of said monoclonal antibody to the terminal epitope of the C5 domain of the a3 chain of collagen type VI in the sample.

7. The method as claimed in claim 6, wherein said method further comprises quantifying the amount of said C-terminal epitope of the a3 chain of collagen type VI in the sample, wherein the sample is a biofluid.

8. The method as claimed in claim 7, wherein said biofluid is serum, plasma, urine or amniotic fluid.

9. The method as claimed in claim 6, wherein said immunoassay is a competition assay or a sandwich assay.

10. The method as claimed in claim 9, wherein said immunoassay is a radioimmunoassay or an enzyme-linked immunosorbent assay.

11. An immunoassay assay kit for determining the quantity of a C-terminal epitope of the C5 domain of the a3 chain of collagen Type VI in a biological sample, comprising: the isolated monoclonal antibody of claim 1 and at least one of: a streptavidin coated 96 well plate, a biotinylated peptide wherein the peptide has an amino acid sequence as set forth in SEQ ID. NO:1, an optionally biotinylated secondary antibody for use in a sandwich immunoassay; a calibrator peptide comprising an amino acid sequence as set forth in SEQ ID. NO:1, an antibody HRP labeling kit, an antibody radiolabeling kit; and an assay visualization kit.

* * * * *